United States Patent
Stahl et al.

(10) Patent No.: US 12,215,077 B2
(45) Date of Patent: Feb. 4, 2025

(54) METHODS OF DEPOLYMERIZING LIGNIN

(71) Applicant: Wisconsin Alumni Research Foundation, Madison, WI (US)

(72) Inventors: Shannon Stahl, Madison, WI (US); Hao Luo, Decatur, IL (US)

(73) Assignee: Wisconsin Alumni Research Foundation, Madison, WI (US)

( * ) Notice: Subject to any disclaimer, the term of this patent is extended or adjusted under 35 U.S.C. 154(b) by 568 days.

(21) Appl. No.: 17/436,202

(22) PCT Filed: Mar. 6, 2020

(86) PCT No.: PCT/US2020/021336
§ 371 (c)(1),
(2) Date: Sep. 3, 2021

(87) PCT Pub. No.: WO2020/181171
PCT Pub. Date: Sep. 10, 2020

(65) Prior Publication Data
US 2022/0127217 A1      Apr. 28, 2022

Related U.S. Application Data

(60) Provisional application No. 62/814,503, filed on Mar. 6, 2019.

(51) Int. Cl.
*C07C 51/31* (2006.01)
*B01J 31/18* (2006.01)
(Continued)

(52) U.S. Cl.
CPC ........... *C07C 51/313* (2013.01); *B01J 31/183* (2013.01); *B01J 35/56* (2024.01); *C07C 45/59* (2013.01)

(58) Field of Classification Search
CPC ........ C07C 51/313; C07C 45/59; B01J 35/56; B01J 31/183
See application file for complete search history.

(56) References Cited

U.S. PATENT DOCUMENTS

2014/0249300 A1    9/2014   Bozell et al.
2020/0317593 A1*  10/2020   Klein ................. B01D 11/0219

FOREIGN PATENT DOCUMENTS

WO    WO-2013173316 A1 *  11/2013  ............... C08H 6/00
WO    2017/171652 A1      10/2017

OTHER PUBLICATIONS

Diaz-Urrutia, C., et al., Towards lignin valorisatin: comparing homogeneous catalyst fro the aerobic oxidation and depolymerisatin of organosolv lignin, RCS Advances, vol. 5, pp. 70502-70511 (Year: 2015).*

(Continued)

*Primary Examiner* — Yate' K Cutliff
(74) *Attorney, Agent, or Firm* — Daniel A. Blasiole; DeWitt LLP

(57) ABSTRACT

Methods of depolymerizing lignin and products obtained therefrom. The methods include reacting lignin in a liquid solvent comprising an oxidation catalyst with the solvent being in contact with $O_2$ gas. The solvent can include aprotic polar solvents. The oxidation catalyst can include heterogeneous catalysts. The methods can be used in the oxidative catalytic fractionation of raw biomass to generate soluble aromatic monomers and a solid carbohydrate residue. Depolymerized lignin products include phenolic and benzoquinone monomers, such as p-hydroxybenzoic acid, vanillin, syringaldehyde, vanillic acid, and/or syringic acid.

33 Claims, 13 Drawing Sheets

(51) Int. Cl.
B01J 35/56 (2024.01)
C07C 45/59 (2006.01)

(56) References Cited

OTHER PUBLICATIONS

Chan, J.M.W., et al., Studies on the vanadium-catalyzed nonoxidative depolymerization of Miscanthus giganteus-derived lignin, ASC Catalysis, vol. 3, pp. 1269-1377 (Year: 2013).*
International Search Report and Written Opinion on PCT Application No. PCT/US2020/21336 dated Jun. 19, 2020.
Ali, Md. E.; Rahman, Md. M.; Sarkar, S. M.; Hamid, S. B. A., Heterogeneous Metal Catalysts for Oxidation Reactions. Journal of Nanomaterials 2014, Article ID 192038, pp. 1-23.
Anderson, E. M. et al. Flowthrough Reductive Catalytic Fractionation of Biomass. Joule 1, 613-622 (2017).
Anderson, E. M., Stone, M. L., Hulsey, M. J., Beckham, G. T. & Roman-Leshkov, Y. Kinetic Studies of Lignin Solvolysis and Reduction by Reductive Catalytic Fractionation Decoupled in Flow-Through Reactors. ACS Sustainable Chem. Eng. 6, 7951-7959 (2018).
Barth, T.; Kleinert, M., Motor fuels from biomass pyrolysis. Chemical Engineering & Technology: Industrial Chemistry—Plant Equipment—Process Engineering—Biotechnology 2008, 31 (5), 773-781.
Beckham, G. T., Johnson, C. W., Karp, E. M., Salvachua, D. & Vardon, D. R. Opportunities and challenges in biological lignin valorization. Curr. Opin. Biotech. 42, 40-53 (2016).
Behling, R., Valange, S. & Chatel, G. Heterogeneous catalytic oxidation for lignin valorization into valuable chemicals: what results? What limitations? What trends? Green Chem. 18, 1839-1854 (2016).
Bosque, I., Magallanes, G., Rigoulet, M., Karkas, M. D. & Stephenson, C. R. J. Redox Catalysis Facilitates Lignin Depolymerization. ACS Cent. Sci. 3, 621-628 (2017).
Cheng et al. Catalytic Oxidation of Lignin in Solvent Systems for Production of Renewable Chemicals: A Review, Polymers, vol. 9, 240 (2014).
Choi, Jong-Ho. (2013). Synthesis and Characterization of Nonprecious Metal Co-PANI-C Catalysts for Polymer Electrolyte Membrane Fuel Cell Cathodes. Journal of the Korean Electrochemical Society. 16. 10.5229/JKES.2013.16.1.52-58.
Das, A. et al. Lignin Conversion to Low-Molecular-Weight Aromatics via an Aerobic Oxidation-Hydrolysis Sequence: Comparison of Different Lignin Sources. ACS Sustainable Chem. Eng. 6, 3367-3374 (2018).
Diaz-Urrutia et al. Towards lignin valorisation: comparing homogeneous catalysts for the aerobic oxidation and depolymerization of organosolv ligin. RSC Advances, vol. 5, 70502-70511, (2015).
Elangovan, S. et al. From Wood to Tetrahydro-2-benzazepines in Three Waste-Free Steps: Modular Synthesis of Biologically Active Lignin-Derived Scaffolds. ACS Cent. Sci. 5, 1707-1716 (2019).
Gewirth, A. A.; Varnell, J. A.; and DiAscro, A. M., Nonprecious Metal Catalysts for Oxygen Reduction in Heterogeneous Aqueous Systems. Chemical Reviews, 2018, 118, 2313-2339.
Hanson, S. K.; Baker, R. T., Knocking on wood: base metal complexes as catalysts for selective oxidation of lignin models and extracts. Accounts of chemical research 2015, 48 (7), 2037-2048.
He, L., Weniger, F., Neumann, H. & Beller, M. Synthesis, Characterization, and Application of Metal Nanoparticles Supported on Nitrogen-Doped Carbon: Catalysis beyond Electrochemistry. Angew. Chem. Int. Ed. 55, 12582-12594 (2016).
Huang, X. et al. Reductive fractionation of woody biomass into lignin monomers and cellulose by tandem metal triflate and Pd/C catalysis. Green Chem. 19, 175-187 (2017).
Jafari, Y., Amiri, H. & Karimi, K. Acetone pretreatment for improvement of acetone, butanol, and ethanol production from sweet sorghum bagasse. Appl. Energy 168, 216-225 (2016).

Jagadeesh, R. V. et al. Selective Oxidation of Alcohols to Esters Using Heterogeneous Co3O4-N@C Catalysts under Mild Conditions. J. Am. Chem. Soc, 135, 10776-10782 (2013).
Kaur, N. & Kishore, Metal and Non-metal Based Catalysts for Oxidation of Organic Compounds D. Catal Surv Asia 2013, 17 (1), 20-42.
Key, R. E.; Bozell, J. J., Progress toward lignin valorization via selective catalytic technologies and the tailoring of biosynthetic pathways. Acs Sustain Chem Eng 2016, 4 (10), 5123-5135.
Klein, I., Marcum, C., Kenttamaa, H. & Abu-Omar, M. M. Mechanistic investigation of the Zn/Pd/C catalyzed cleavage and hydrodeoxygenation of lignin. Green Chem. 18, 2399-2405 (2016).
Koelewijn, S.-F. et al. Promising bulk production of a potentially benign bisphenol a replacement from a hardwood lignin platform. Green Chem. 20, 1050-1058 (2018).
Kumaniaev, I. et al. Lignin depolymerization to monophenolic compounds in a flowthrough system. Green Chem. 19, 5767-5771 (2017).
Kumar, P.; Barrett, D. M.; Delwiche, M. J.; Stroeve, P., Methods for Pretreatment of Lignocellulosic Biomass for Efficient Hydrolysis and Biofuel Production. Industrial & Engineering Chemistry Research 2009, 48, (8), 3713-3729.
Kumar AK and Sharma S. Recent Updates on Different Methods of Pretreatment of Lignocellulosic Feedstocks: A Review. Bioresour. Bioprocess. (2017) 4:7.
Langholtz, M. H., Stokes, B. J. & Eaton, L. M. 2016 Billion-Ton Report: Advancing Domestic Resources for a Thriving Bioeconomy, vol. 1: Economic Availability of Feedstocks . . . U.S. Department of Energy, Oak Ridge National Laboratory, Oak Ridge, TN. (2016). doi: 10.2172/1271651.
Lancefield, C. S., Ojo, O. S., Tran, F. & Westwood, N. J. Isolation of Functionalized Phenolic Monomers through Selective Oxidation and C—O Bond Cleavage of the (β-0-4 Linkages in Lignin. Angew. Chem. Int. Ed. 54, 258-262 (2015).
Li, C., Zheng, M., Wang, A. & Zhang, T. One-pot catalytic hydrocracking of raw biomass into chemicals over supported carbide catalysts; simultaneous conversion of cellulose, hemicellulose, and lignin. Energy Environ. Sci. 5, 6383-6390 (2012).
Li, C., Zhao, X., Wang, A., Huber, G. W. & Zhang, T. Catalytic Transformation of Lignin for the Production of Chemicals and Fuels. Chem. Rev. 115, 11559-11624 (2015).
Liu, S. et al. Oxidative cleavage of (β-0-4 bonds in lignin model compounds with a single-atom Co catalyst. Green Chem. 21, 1974-1981 (2019).
Llevot, A., Grau, E., Carlotti, S., Grelier, S. & Cramail, H. From Lignin-derived Aromatic Compounds to Novel Biobased Polymers. Macromol. Rapid Comm. 37, 9-28 (2016).
Lora, J. Industrial Commercial Lignins: Sources, Properties and Applications, in Monomers, Polymers and Composites from Renewable Resources (eds. Belgacem, M. N. & Gandini, A.) 225-241 (Elsevier Ltd., 2008).
Luo, H. et al. Total Utilization of Miscanthus Biomass, Lignin and Carbohydrates, Using Earth Abundant Nickel Catalyst. ACS Sustainable Chem. Eng. 4, 2316-2322 (2016).
Luo, H.; Abu-Omar, M. M., Lignin extraction and catalytic upgrading from genetically modified poplar. Green Chem 2018, 20 (3), 745-753.
Luo, H.; Wang L. et al. Nitrogen-Doped Carbon-Modified Cobalt-Nanoparticle-Catalyzed Oxidative Cleavage of Lignin (β-0-4 Model Compounds under Mild Conditions. ACS Sustainable Chem. Eng. 6, 14188-14196 (2018).
Ma, R., Xu, Y. & Zhang, X. Catalytic Oxidation of Biorefinery Lignin to Value-added Chemicals to Support Sustainable Biofuel Production. ChemSusChem 8, 24-51 (2015).
Mallat, T. & Baiker, A. Oxidation of Alcohols with Molecular Oxygen on Solid Catalysts. Chem. Rev. 104, 3037-3058 (2004).
McKendry, P. Energy production from biomass (part 1): overview of biomass. Bioresource Technol. 83, 37-46 (2002).
Mosier, N. et al. Features of promising technologies for pretreatment of lignocellulosic biomass. Bioresource Technol. 96, 673-686 (2005).

(56) References Cited

OTHER PUBLICATIONS

Osterberg, P. et al. Experimental Limiting Oxygen Concentrations for Nine Organic Solvents at Temperatures and Pressures Relevant to Aerobic Oxidations in the Pharmaceutical Industry. Org. Process Res. Dev. 19, 1537-1543 (2015).

Parsell, T. et al. A synergistic biorefinery based on catalytic conversion of lignin prior to cellulose starting from lignocellulosic biomass. Green Chem. 17, 1492-1499 (2015).

Perez, J. M. et al. Funneling aromatic products of chemically depolymerized lignin into 2-pyrone-4-6-dicarboxylic acid with Novosphingobium aromaticivorans. Green Chem. 21, 1340-1350 (2019).

Perras, F. d. r. A.; Luo, H.; Zhang, X.; Mosier, N. S.; Pruski, M.; Abu-Omar, M. M., Atomic-level structure characterization of biomass pre-and post-lignin treatment by dynamic nuclear polarization-enhanced solid-state NMR. The Journal of Physical Chemistry A 2017, 121 (3), 623-630.

Preger, Y. et al. Quinone-Mediated Electrochemical O2 Reduction Accessing High Power Density with an Off-Electrode Co—N/C Catalyst. Joule 2, 2722-2731 (2018).

Rafiee, M., Alherech, M., Karlen, S. D. & Stahl, S. S., Electrochemical Aminoxyl-Mediated Oxidation of Primary Alcohols in Lignin to Carboxylic Acids: Polymer Modification and Depolymerization, J. Am. Chem. Soc, 141, 15266-15276 (2019).

Ragauskas, A. J.; Williams, C. K.; Davison, B. H.; Britovsek, G.; Cairney, J.; Eckert, C. A.; Frederick, W. J.; Hallett, J. P.; Leak, D. J.; Liotta, C. L., Mielenz, J. R., Murphy, R., Templer, R., Tschaplinski, T. The path forward for biofuels and biomaterials. Science 2006, 311 (5760), 484-489.

Ragauskas, A. J. et al. Lignin Valorization: Improving Lignin Processing in the Biorefinery. Science, 344, 1246843 (2014).

Rahimi, A., Azarpira, A., Kim, H., Ralph, J. & Stahl, S. S. Chemoselective Metal-Free Aerobic Alcohol Oxidation in Lignin. J. Am. Chem. Soc. 135, 6415-6418 (2013).

Rahimi, A., Ulbrich, A., Coon, J. J. & Stahl, S. S. Formic-acid-induced depolymerization of oxidized lignin to aromatics. Nature 515, 249-252 (2014).

Renders, T., Van den Bosch, S., Koelewijn, S.-F., Schutyser, W. & Sels, B. F. Lignin-first biomass fractionation: the advent of active stabilisation strategies. Energy Environ. Sci. 10, 1551-1557 (2017).

Renders, T., Van den Bossche, G., Vangeel, T., Van Aelst, K. & Sels, B. Reductive catalytic fractionation: state of the art of lignin-first biorefinery. Curr. Opin. Biotech. 56, 193-201 (2019).

Rinaldi, R. et al. Paving the Way for Lignin Valorisation: Recent Advances in Bioengineering, Biorefining and Catalysis. Angew. Chem. Int. Ed. 55, 8164-8215 (2016).

Sagues, W. J.; Bao, H.; Nemenyi, J. L.; Tong, Z., Lignin-First Approach to Biorefining: Utilizing Fenton's Reagent and Supercritical Ethanol for the Production of Phenolics and Sugars. Acs Sustain Chem Eng 2018, 6 (4), 4958-4965.

Schutyser, W.; Renders, T.; Van den Bosch, S.; Koelewijn, S.-F.; Beckham, G. T.; Sels, B. F.. Chemicals from lignin: an interplay of lignocellulose fractionation, depolymerisation, and upgrading. Chem. Soc. Rev. 47, 852-908 (2018).

Schutyser, W.; Kruger, J. S.; Robinson, A. M.; Katahira, R.; Brandner, D. G.; Cleveland, N. S.; Mittal, A.; Peterson, D. J.; Meilan, R.; Roman-Leshkov, Y.. Revisiting alkaline aerobic lignin oxidation. Green Chem. 20, 3828-3844 (2018).

Sluiter, A. et al. Determination of Structural Carbohydrates and Lignin in Biomass, Laboratory Analytical Procedure. 2012. NREL Technical Report NREL/TP-510-42618. National Renewable Energy Laboratory, Office of Energy Efficiency and Renewable Energy, U.S. Department of Energy.

Smit, A. & Huijgen, W. Effective fractionation of lignocellulose in herbaceous biomass and hardwood using a mild acetone organosolv process. Green Chem. 19, 5505-5514 (2017).

Song, Q. et al. Lignin depolymerization (LDP) in alcohol over nickel-based catalysts via a fragmentation-hydrogenolysis process. Energy Environ. Sci. 6, 994-1007 (2013).

Song, Y. et al. Gold-catalyzed conversion of lignin to low molecular weight aromatics, Chem. Sci. 9, 8127-8133 (2018).

Strassberger, Z., Tanase, S. & Rothenberg, G. The pros and cons of lignin valorization in an integrated biorefinery. RSC Adv. 4, 25310-25318 (2014).

Sun, T. Tian, B. Su, C. Recent advances in Fe (or Co)/N/C electrocatalysts for the oxygen reduction reaction in polymer electrolyte membrane fuel cells. J. Mater. Chem. A. 5, 18933-18950 (2017).

Sun, Z., Fridrich, B., de Santi, A., Elangovan, S. & Barta, K. Bright Side of Lignin Depolymerization: Toward New Platform Chemicals. Chem. Rev. 118, 614-678 (2018).

Tarabanko, V. E., Kaygorodov K.L., et al. Processing pine wood into vanillin and glucose by sequential catalytic oxidation and enzymatic hydrolysis. J. Wood Chem. Tech. 37, 43-51 (2017).

Tarabanko, V. E. & Tarabanko, N. Catalytic Oxidation of Lignins into the Aromatic Aldehydes: Genergal Process Trends and Development Prospects. Int. J. Mol. Sci. 18, 2421-2450 (2017).

Tuck, C. O., Perez, E., Horvath, I. T., Sheldon, R. A. & Poliakoff, M. Valorization of Biomass: Deriving More Value from Waste. Science 337, 695-699 (2012).

Upton, B. M.; Kasko, A. M., Strategies for the conversion of lignin to high-value polymeric materials: review and perspective. Chem Rev 2015, 116 (4), 2275- 2306.

Van den Bosch, S. et al. Integrating lignin valorization and bio-ethanol production: on the role of Ni-Al2O3 catalyst pellets during lignin-first fractionation. Green Chem. 19, 3313-3326 (2017).

Vangeel, T., Schutyser, W., Renders, T. & Sels, B. F. Perspective on Lignin Oxidation: Advances, Challenges, and Future Directions. Top. Curr. Chem. 376, 30 (2018).

Wang, S., Shuai, L., Saha, B., Vlachos, D. G. & Epps, T. H., III. From Tree to Tape: Direct Synthesis of Pressure Sensitive Adhesives from Depolymerized Raw Lignocellulosic Biomass. ACS Cent. Sci. 2018, 701-708 (2018).

Wu, G.; More, K. L.; Johnston, C. M.; Zelenay, P., High-Performance Electrocatalysts for Oxygen Reduction Derived from Polyaniline, Iron, and Cobalt. Science 2011 332, 443-447.

\* cited by examiner

| biomass sources | solvents | catalysts |
|---|---|---|
| • hardwoods | • polar aprotic | • metal oxides |
| • softwoods | • polar protic | • M-N/C |
| • grasses | • water | • PGM/C | raw biomass post-OCF residue acid hydrolysis of carbohydrate residue p-hydroxybenzoic acid vanillic acid vanillin syringic acid syringaldehyde acetovanillone acetosyringone propylvanillone propylsyringone β-hydroxypropiovanillone β-methoxypropiovanillone β-hydroxypropiosyringone β-methoxypropiosyringone 1-(4-hydroxy-3-methoxyphenyl)-1,2-propanedione 1-(4-hydroxy-3,5-dimethoxyphenyl)-1,2-propanedione R = H, OH, alkoxy (e.g., C1-C6)

R = H, OH, alkoxy (e.g., C1-C6)

p-hydroxybenzoic acid alkyl ester (R = alkyl (e.g., C1-C6))

vanillic acid alkyl ester (R = alkyl (e.g., C1-C6))

syringic acid alkyl ester (R = alkyl (e.g., C1-C6))

p-hydroxybenzaldehyde 2,6-dimethoxybenzoquinone

METHODS OF DEPOLYMERIZING LIGNIN

STATEMENT REGARDING FEDERALLY SPONSORED RESEARCH

This invention was made with government support under DE-SC0018409 awarded by the US Department of Energy. The government has certain rights in the invention.

FIELD OF THE INVENTION

The invention is directed to methods of depolymerizing lignin, including the oxidative catalytic fractionation of biomass, and products obtained therefrom.

BACKGROUND

Lignocellulosic biomass is one of the promising renewable energy sources with great potential for generating value-added chemicals which can help reduce our reliance on fossil fuels. Major components of biomass including cellulose (35-50%), hemicellulose (25-30%) and lignin (15-25%) (Sagues et al. 2018). Lignin as the second largest reservoir of carbon (after carbohydrate) accounts for about 30% of organic carbon in biosphere and 40% of the energy in biomass (Upton et al. 2015, Luo and Abu-Omar et al. 2018). Lignin is a structurally complex heterogeneous aromatic biopolymer made of three principal building blocks, p-hydroxyphenol (H), guaiacyl (G) and syringyl (S) units. It is the largest renewable source of aromatic building blocks in nature, and represents huge potential for deriving high value aromatic compounds which can be applied as transportation fuels, bio-based polymer materials and well-defined chemicals, etc. (Sagues et al. 2018, Ragauskas et al. 2006, Barth et al. 2008, Sun et al. 2018). Unfortunately, lignin has been traditionally treated as waste and burnt for its heat value due to the very complex structure and less developed techniques.

In the past few decades, various lignin depolymerization strategies have been developed, which can be generally categorized as: reductive, oxidative, acid-catalyzed, base-catalyzed, thermal methods, etc. (Sun et al. 2018, Behling et al. 2016, Li et al. 2015, Schutyser and Kruger et al. 2018). In general, a depolymerization process breaks the interunit linkages within the lignin macromolecule, converting complex lignin polymers into oligomers or monomeric aromatic products to be upgraded to specialty fuels and chemicals. Among different treatments, lignin oxidative depolymerization presents advantages in making aromatic compounds with oxygen-containing functional groups. Currently, lignin oxidation research has been extensively examined on model compounds, with less attention focused on isolated lignin samples (Schutyser and Renders et al. 2018). However, these lignin model compounds are less representative due to their simplified structure compared to the high complexity of real lignin. On the other hand, lignin extraction process usually leads to a recovery of only 30-70% of the original lignin contained in raw biomass, and often causes damage to the lignin structure, which results in less promising behavior towards further depolymerization to monomers.

Strategies that facilitate efficient oxidative depolymerization of lignin in intact, untreated biomass are highly desirable.

SUMMARY OF THE INVENTION

One aspect of the invention is directed to methods of depolymerizing lignin. The methods can comprise reacting in a liquid solvent the lignin and an oxidation catalyst with the solvent being in contact with gas comprising $O_2$ gas.

In some versions, the solvent comprises organic solvent. In some versions, the solvent comprises aprotic solvent. In some versions, the solvent comprises aprotic solvent in an amount of at least about 90% v/v. In some versions, the aprotic solvent is a polar aprotic solvent. In some versions, the solvent is devoid of protic solvent or comprises protic solvent in an amount less than about 10% v/v. In some versions, the solvent is selected from the group consisting of acetone, acetonitrile, and a combination thereof. In some versions, the solvent comprises a solvent that is not an alcohol and is not water.

In some versions, the oxidation catalyst is a heterogeneous catalyst. In some versions, the oxidation catalyst is a metal-based catalyst. In some versions, the oxidation catalyst comprises a metal-containing nitrogen-doped carbon catalyst. In some versions, the oxidation catalyst comprises a metal other than palladium and ruthenium. In some versions, the oxidation catalyst comprises a non-noble metal. In some versions, the oxidation catalyst comprises a first-row transition metal. In some versions, the oxidation catalyst comprises a metal selected from the group consisting of Mn, Fe, Co, Ni, V, and Cu. In some versions, the oxidation catalyst is comprised in the solvent within a porous cage.

In some versions, the gas comprises $O_2$ gas in an amount from about 1% v/v to about 10% v/v. In some versions, the $O_2$ gas is present at a partial pressure of from about 1 to about 3 bar.

In some versions, the reacting is conducted at a temperature from about 100° C. to about 240° C.

In some versions, the lignin is in the form of lignocellulosic biomass. In some versions, the lignin is in the form of lignocellulosic biomass comprising the lignin and at least one of cellulose and hemicellulose. In some versions, the lignin is in the form of lignocellulosic biomass comprising the lignin in an amount from about 10% w/w to about 80% w/w of the lignocellulosic biomass and at least one of cellulose in an amount from about 5% w/w to about 90% w/w of the lignocellulosic biomass and hemicellulose in an amount from about 5% w/w to about 90% w/w of the lignocellulosic biomass. In some versions, the lignin is in the form of raw lignocellulosic biomass. In some versions, the lignin is in the form of lignocellulosic biomass that has not been treated with any one or more of chemical pretreatment and physicochemical pretreatment.

In some versions, the reacting is conducted for a time from about 4 hours to about 16 hours. In some versions, the reacting is conducted for a time sufficient to produce a phenolic or benzoquinone monomer. In some versions, the reacting is conducted for a time sufficient to produce a phenolic monomer comprising a benzylic carbonyl. In some versions, the reacting is conducted for a time sufficient to produce p-hydroxybenzoic acid, vanillin, syringaldehyde, vanillic acid, and/or syringic acid.

Some versions further comprise, after the reacting, separating a carbohydrate residue produced during the reacting from the solvent. Some versions further comprise, after the reacting, isolating a phenolic monomer produced during the reacting from the solvent.

The objects and advantages of the invention will appear more fully from the following detailed description of the preferred embodiment of the invention made in conjunction with the accompanying drawings.

BRIEF DESCRIPTION OF THE DRAWINGS

FIG. 2A. Traditional cellulosic biomass isolation approaches focusing on obtaining high-quality carbohydrates. FIG. 2B. Redox catalytic fractionation (such as reductive catalytic fractionation and oxidative catalytic fractionation), focused on obtaining high-quality carbohydrates and lignin-derived aromatic monomers. FIG. 2C. Identity of monomers primarily produced from reductive catalytic fractionation. FIG. 2D. Identity of exemplary monomers produced via exemplary versions of the oxidative catalytic fractionation of the present invention.

FIG. 3A. HPLC program showing the gradient of acetonitrile percentage (B.Conc) used to determine monomer yields. Solvent A was 0.1% formic acid in water. FIG. 3B. HPLC program showing the gradient of acetonitrile percentage (B.Conc) used to separate the lignin-derived oligomers. Solvent A was 0.1 formic acid in water.

FIG. 4A. Schematic of oxidative catalytic fractionation reactor. FIG. 4B. Examples of some of the tested variables. Biomass sources include hardwoods (poplar, birch), softwoods (pine), and grasses (miscanthus). Solvents tested include polar aprotic solvents (e.g. acetone, acetonitrile, ethyl acetate), polar protic solvents (e.g. methanol), and water. Catalysts tested include metal oxides, metal on nitrogen-doped carbon (M-N/C) catalysts, and supported platinum-group metal (PGM/C) catalysts.

FIG. 11A. 1D $^{13}C$ CPMAS NMR spectra of raw biomass. FIG. 11B. 1D $^{13}C$ CPMAS NMR spectra of carbohydrate residue post-oxidative catalytic fractionation (OCF). FIG. 11C. Acid hydrolysis of carbohydrate residue to glucose and xylose following a modified NREL procedure.

DETAILED DESCRIPTION OF THE INVENTION

Figure 1:
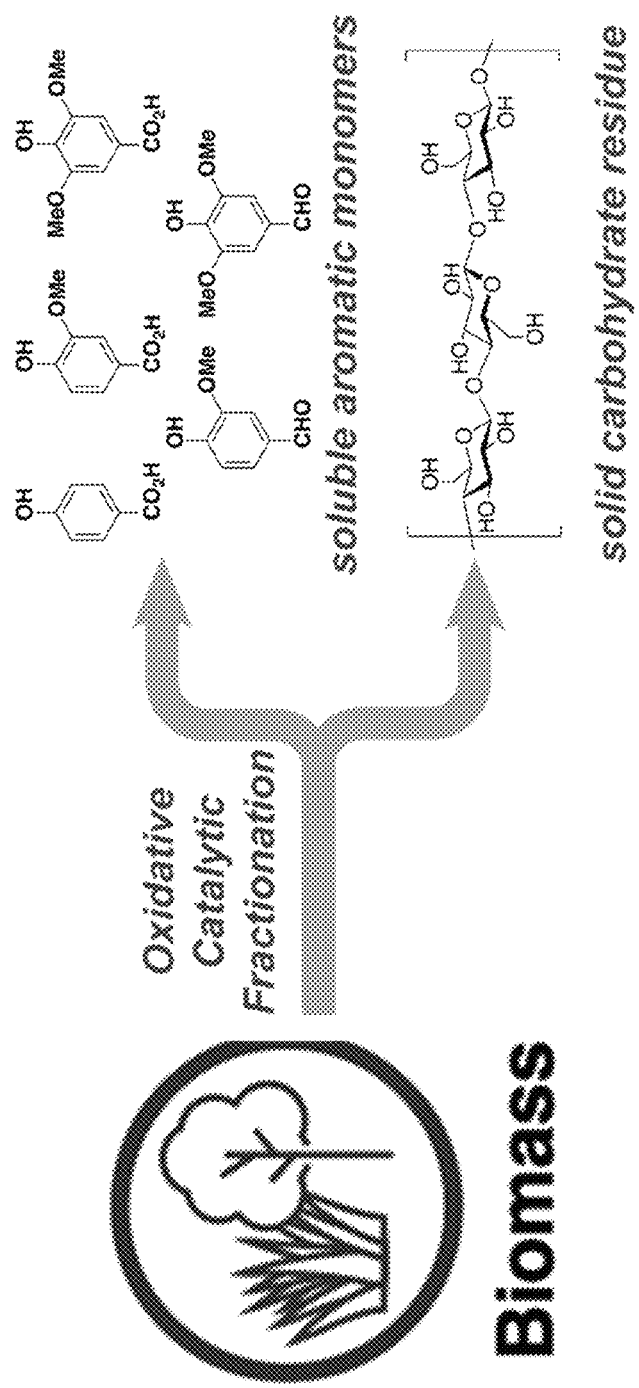
FIG. 1. Schema of an oxidative catalytic fractionation method of the present invention.

One aspect of the invention is directed to methods of depolymerizing lignin. The methods can comprise reacting in a liquid solvent the lignin and an oxidation catalyst with the solvent being in contact with gas comprising $O_2$ gas.

The term "solvent" is used broadly to refer to any liquid medium for the depolymerization reaction. The solvent can comprise a polar solvent, a non-polar solvent, an organic solvent, an inorganic solvent, a protic solvent, an aprotic solvent, or any combination thereof.

In some versions of the invention, the solvent comprises or consists of organic solvent. The solvent in some versions can comprise the organic solvent in an amount from about 1% v/v to about 100% v/v, such as an amount of at least about 1% v/v, at least about 5% v/v, at least about 10% v/v, at least about 15% v/v, at least about 20% v/v, at least about 25% v/v, at least about 30% v/v, at least about 35% v/v, at least about 40% v/v, at least about 45% v/v, at least about 50% v/v, at least about 55% v/v, at least about 60% v/v, at least about 70% v/v, at least about 75% v/v, at least about 80% v/v, at least about 85% v/v, at least about 90% v/v, at least about 95% v/v, or at least about 99% v/v.

In some versions of the invention, the solvent comprises or consists of an aprotic solvent. As understood in the art, aprotic solvents are solvents that have no O—H or N—H bonds. Non-limiting examples of aprotic solvents include dichloromethane (DCM), N-methylpyrrolidone, tetrahydrofuran (THF), ethyl acetate (EtOAc), acetone, dimethylformamide (DMF), hexamethylphosphoramide (HMPA), acetonitrile (MeCN), dimethyl sulfoxide (DMSO), gamma-valerolactone (GVL), dimethyl carbonate, and propylene carbonate. The solvent in some versions can comprise the aprotic solvent in an amount from about 1% v/v to about 100% v/v, such as an amount of at least about 1% v/v, at least about 5% v/v, at least about 10% v/v, at least about 15% v/v, at least about 20% v/v, at least about 25% v/v, at least about 30% v/v, at least about 35% v/v, at least about 40% v/v, at least about 45% v/v, at least about 50% v/v, at least about 55% v/v, at least about 60% v/v, at least about 70% v/v, at least about 75% v/v, at least about 80% v/v, at least about 85% v/v, at least about 90% v/v, at least about 95% v/v, or at least about 99% v/v. In preferred versions of the invention, the solvent comprises the aprotic solvent in an amount of at least about 90% v/v, at least about 95% v/v, or at least about 99% v/v. The aprotic solvent is preferably a polar aprotic solvent.

In some versions, the solvent is devoid of protic solvent or contains protic solvent in an amount less than 100% v/v, such as an amount less than about 99% v/v, less than about 95% v/v, less than about 90% v/v, less than about 85% v/v, less than about 80% v/v, less than about 75% v/v, less than about 70% v/v, less than about 65% v/v, less than about 60% v/v, less than about 55% v/v, less than about 50% v/v, less than about 45% v/v, less than about 40% v/v, less than about 35% v/v, less than about 30% v/v, less than about 25% v/v, less than about 20% v/v, less than about 15% v/v, less than about 10% v/v, less than about 5% v/v, or less than about 1% v/v. In preferred versions of the invention, the solvent is devoid of protic solvent or contains protic solvent in an amount less than about 10% v/v, less than about 5% v/v, or less than about 1% v/v.

In some versions of the invention, the solvent comprises a solvent that is not an alcohol and is not water. In some versions, the solvent is devoid of water, alcohol, or water and alcohol. In some versions, the solvent is selected from the group consisting of acetone, acetonitrile, and a combination thereof.

The oxidation catalyst can include any catalyst capable of catalyzing an oxidation reaction. The oxidation catalyst can include a metal-based catalyst, a non-metal-based catalyst, a homogeneous catalyst, a heterogeneous catalyst, or any combination thereof. See Kaur et al. 2013 for examples of metal-based catalysts and non-metal-based catalysts.

In some versions of the invention, the oxidation catalyst is a heterogeneous catalyst. Nonlimiting examples of heterogeneous oxidation catalysts include Co-PANI-C, Fe-PANI-C, PANI-FeCo—C, Co-Phen-C, $Co_3O_4$, $Fe_2O_3$, $Mn_2O_3$ or other manganese oxides, CuO, Pd/C, Pt/C, Ru/C, Ni/C, Fe nanocatalyst, other metal on nitrogen-doped carbon (M-N/C) catalysts containing Fe or Co (for example, such as those used for electrochemical dioxygen reduction, see Sun et al. 2017 or Gewirth et al. 2018), $Fe_2O_3$ on silica, $Al_2O_3$, $TiO_2$, or other metal-oxide support, $Co_3O_4$ on silica, $Al_2O_3$, $TiO_2$, or other metal oxide support, supported Fe, Co, Ni, Cu or Mn phthalocyanines or porphyrins, vanadium oxides, Fe, Co, Ni, Cu, or Mn in zeolites such as ZSM-5, $MnO_x$ on alumina, mixed Mn—Co oxides, $Au/Al_2O_3$, Au/C, Au/Pt bimetallic nanoparticles, gold nanoparticles supported on $Mg(OH)_2$ nano sheets, $Au/TiO_2$ supported on ferritic stainless steel monoliths, nanoporous gold, P123-stabilized Au—Ag alloy, alumina-supported gold-ruthenium bimetallic catalysts, Au/CuO catalysts, cerium modified silver, Pd-Au catalyst, Au/ZnO, $Au/TiO_2$, microstructured Au/Ni-fiber, nanocrystalline Ag and Au—Ag alloys supported on titania, nanosized Au supported on 3-D ordered mesoporous $MnO_2$, $Au/FeO_x$, nanosized ruthenium particles decorated carbon nanofibers, Au/C, CeAl PO-5 molecular sieves, nanosized gold on $SiO_2$, $Au/SiO_2$, nano gold-mesoporous silica, nanosized gold, Ag/SBA-15, bimetallic Au-Pd/MgO, inverse $Fe_2O_3$/Au(111) model catalysts, silica-supported Au—Cu alloy, gold nanoparticles supported on MgO, silica-supported Au—$CuO_x$, $Au/Al_2O_3$, Au—Pd/C, Pd-Te supported catalysts, gold nanoparticles supported on functionalized mesoporous silica, silica supported cobalt (II) salen complex, gold nanowires, $Cu_{3/2}[PMo_{12}O_{40}]SiO_2$, gold nanoparticles deposited on cellulose, metalloporphyrin bound to silica, hydrophobized palladium, supported gold catalysts, Au/HMS catalysts, mobilized gold nanoparticles, mesoporous $Co_3O_4$, mesoporous and $Au/Co_3O_4$, metal-organic framework supported gold nanoparticles, $Pt/Al_2O_3$, $Au/TiO_2$, $Co(AcO)_2Mn(AcO)_2$, nickel substituted copper chromite spinels, gold catalysts, MCM-48 molecular sieve modified with $SnCl_2$, CuO-impregnated mesoporous silica, Au—$CuO/Al_2O_3$, $Pt/Al_2O_3$, manganese-containing mesoporous MCM-41 and Al-MCM-41 molecular sieves, Au/C, gold immobilized mesoporous silica, nitrous oxide over MFI zeolites, CoAPO-5 molecular sieves, Mn-containing MCM-41, Mn (Salen)/MCM-41, nanostructured $CuO_x/CeO_2$, nano-Au catalysts, heteropoly catalysts containing Ru(III) and Rh(III) particles, gold supported on ZnO and $TiO_2$, bismuth promoted palladium catalysts, or other metal oxides not named above. See Ali et al. 2014 for further details on the above-mentioned catalysts. As used herein, "PANI" is an abbreviation for polyaniline, and "Phen" is an abbreviation for 1,10-phenanthroline.

In some versions, the oxidation catalyst comprises a metal-based catalyst. A metal-based catalyst is a catalyst that comprises a metal. The metal can be any metal described in any catalyst herein. The metal can comprise or consist of a metal other than palladium and ruthenium. The metal can comprise or consist of a non-noble metal. "Non-noble metal" is used herein to refer to a metal that is not a noble metal. "Noble metal" is used herein to refer to ruthenium (Ru), rhodium (Rh), palladium (Pd), silver (Ag), osmium (Os), iridium (Ir), platinum (Pt), and gold (Au). The metal can comprise or consist of a transition metal. The metal can comprise or consist of a first-row transition metal. "First-row transition metal" refers to transition metals in the first row of the periodic table, i.e. scandium (Sc), titanium (Ti), vanadium (V), chromium (Cr), manganese (Mn), iron (Fe), cobalt (Co), nickel (Ni), copper (Cu), and zinc (Zn). In some versions, the metal can comprise or consist of titanium (Ti), vanadium (V), chromium (Cr), manganese (Mn), iron (Fe), cobalt (Co), nickel (Ni), and/or copper (Cu). In some versions, the metal can comprise or consist of manganese (Mn), iron (Fe), cobalt (Co), nickel (Ni), vanadium (V), and/or copper (Cu).

In some versions, the oxidation catalyst comprises a metal-containing nitrogen-doped carbon catalyst. Exemplary metal-containing nitrogen-doped carbon catalysts include metal-PANI/C or metal-Phen/C catalyst. Exemplary metals in the metal-containing nitrogen-doped carbon catalyst include the metals described above for the metal-based catalyst, such as Co and Fe, among others.

In some versions, the oxidation catalyst can comprise a non-metal-based catalyst. A non-metal-based catalyst is a catalyst that does not comprises a metal. Examples of non-metal-based catalysts include metal-free nitrogen-doped carbon.

The oxidation catalyst can comprise a solid support. The solid support can comprise any solid support used for any catalyst described herein. The solid support can comprise silica, carbon, clay, zeolite, nitrogen-containing carbon matrices, polymers (e.g., polyaniline polymers), metal oxides, metal nitrides, boron nitride, and other materials. The supports can be porous. The supports can be microporous (having an average pore diameter of less than 2 nm), mesoporous (having an average pore diameter between 2 nm and 50 nm), or macroporous (having an average pore diameter of greater than 50 nm).

Mesoporous and microporous supports are preferred.

The oxidation catalyst can be confined within a porous cage. The porous cage can be composed of steel alloys, titanium, or other non-reactive metals. The porous cage can have an average pore size of from about 1 µm, about 10 µm, about 50 µm, about 100 µm, about 500 µm, about 1000 µm, or about 2500 µm to about 10 µm, about 50 µm, about 100 µm, about 500 µm, about 1000 µm, about 2500 µm, about 5,000 µm or more. In preferred versions of the invention, the porous cage has an average pore size of from about 10 µm to about 70 µm, such as from about 20 µm to about 60 µm or from about 30 µm to about 50 µm.

The oxidation catalyst in some versions can be included in the solvent in an amount (w catalyst/v solvent) from about 0.001% w/v, about 0.005% w/v, about 0.01% w/v, about 0.05% w/v, 0.1% w/v, about 0.5% w/v, about 1% w/v, about 5% w/v, about 10% w/v, about 15% w/v, about 20% w/v, about 25% w/v, about 30% w/v, about 35% w/v, or about 40% w/v to about 0.005% w/v, about 0.01% w/v, about 0.05% w/v, 0.1% w/v, about 0.5% w/v, about 1% w/v, 5% w/v, about 10% w/v, about 15% w/v, about 20% w/v, about 25% w/v, about 30% w/v, about 35% w/v, about 40% w/v, about 45% w/v, about 50% w/v, or more.

The oxidation catalyst in some versions can be included with the substrate in an amount (w catalyst/w substrate) from about 0.1% w/w, about 0.5% w/w, about 1% w/w, about 5% w/w, about 10% w/w, about 15% w/w, about 20% w/w, about 25% w/w, about 30% w/w, about 35% w/w, or about 40% w/w to about 5% w/w, about 10% w/w, about 15% w/w, about 20% w/w, about 25% w/w, about 30% w/w, about 35% w/w, about 40% w/w, about 45% w/w, about 50% w/w, or more. In preferred versions of the invention, the oxidation catalyst is included with the substrate in an amount (w catalyst/w substrate) from about 1% w/w to about 30% w/w.

The gas in contact with the solvent comprises $O_2$ gas as an oxidant for the reaction. Reference to the gas and liquid solvent being "in contact" indicates that the gas and the liquid solvent persist in different phases and are contiguous with each other along an interface. The gas can be in contact with the solvent by bubbling the gas through the solvent, situating the gas in a headspace over the solvent, or other methods or formats.

The gas in some versions can comprise the $O_2$ gas in an amount from about 0.1% v/v to about 30% v/v or more, such as from about 0.1% v/v, about 0.5% v/v, about 1% v/v, about 5% v/v, about 10% v/v, about 15% v/v, about 20% v/v, or about 25% v/v to about 0.5% v/v, about 1% v/v, about 5% v/v, about 10% v/v, about 15% v/v, about 20% v/v, about 25% v/v, or about 30% v/v. In some versions of the invention, the gas comprises the $O_2$ gas in an amount no greater than about 9% v/v or about 10% v/v. In preferred versions of the invention, the gas comprises the $O_2$ gas in an amount from about 1% v/v to about 10% $O_2$ or from about 1% v/v to about 9% $O_2$.

The balance of the gas beyond the $O_2$ can comprise one or more inert gases. The balance of the gas beyond the $O_2$ can comprise nitrogen. The balance of the gas beyond the $O_2$ can alternatively or additionally comprise one or more noble gases. Noble gases include helium (He), neon (Ne), argon (Ar), krypton (Kr), xenon (Xe), and radon (Rn).

The concentration of the $O_2$ within the gas is preferably below the limiting oxygen concentration (LOC). The limiting oxygen concentration, also known as the minimum oxygen concentration (MOC), is the limiting concentration of oxygen below which combustion is not possible, independent of the concentration of fuel.

The reacting in some versions is conducted with a partial pressure of $O_2$ of from about 1 bar to about 5 bar or more, such as from about 1 bar to about 4 bar, from about 1 bar to about 3 bar, about 1.5 bar to about 2.5 bar, or about 2 bar.

The reacting in some versions can be conducted at a temperature from about 25° C. to about 250° C. or more, such as from about 25° C., about 50° C., about 75° C., about 100° C., about 125° C., about 150° C., about 175° C., or about 200° C. to about 50° C., about 75° C., about 100° C., about 125° C., about 150° C., about 175° C., about 200° C., or about 250° C. In some versions of the invention, the reacting is conducted at a temperature no greater than about 240° C. Preferred temperature ranges include from about 100° C. to about 240° C., such as from about 130° C. to about 230° C., or about 150° C. to about 220° C.

The reacting can be conducted with the solvent being devoid or substantially devoid of strong acid or strong base. Strong acids include hydrochloric acid (HCl), hydrobromic acid (HBr), hydroiodic acid (HI), nitric acid ($HNO_3$), chloric acid ($HClO_3$), perchloric acid ($HClO_4$), and sulfuric acid ($H_2SO_4$). Strong bases include sodium hydroxide (NaOH), lithium hydroxide (LiOH), potassium hydroxide (KOH), rubidium hydroxide (RbOH), cesium hydroxide (CsOH), calcium hydroxide ($Ca(OH)_2$), strontium hydroxide ($Sr(OH)_2$), and barium hydroxide ($Ba(OH)_2$).

The lignin used in the reacting can be in the form of lignocellulosic biomass. The lignocellulosic biomass can comprise the lignin and at least one of cellulose and hemicellulose.

The lignocellulosic biomass in some versions can comprise lignin in an amount from about 1% w/w, about 5% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, about 95% w/w, or about 99% w/w to about 5% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, about 95% w/w, about 99% w/w, or about 100% w/w. In some versions, the lignocellulosic biomass comprises lignin in an amount from about 10% w/w to about 80% w/w, such as about 15% w/w to about 25% w/w.

The lignocellulosic biomass in some versions can comprise cellulose in an amount from about 1% w/w, about 5% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, about 95% w/w, or about 99% w/w to about 5% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, about 95% w/w, about 99% w/w, or about 100% w/w. In some versions, the lignocellulosic biomass comprises cellulose in an amount from about 5% w/w to about 90% w/w, such as about 35% w/w to about 50% w/w.

The lignocellulosic biomass in some versions can comprise hemicellulose in an amount from about 1% w/w, about 5% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, about 95% w/w, or about 99% w/w to about 5% w/w, about 10% w/w, about 15% w/w, about 20% w/w, about 25% w/w, about 30% w/w, about 35% w/w, about 40% w/w, about 45% w/w, about 50% w/w, about 55% w/w, about 60% w/w, about 65% w/w, about 70% w/w, about 75% w/w, about 80% w/w, about 85% w/w, about 90% w/w, about 95% w/w, about 99% w/w, or about 100% w/w. In some versions, the lignocellulosic biomass comprises hemicellulose in an amount from about 5% w/w to about 90% w/w, such as from about 25% w/w to about 30% w/w.

The lignocellulosic biomass can be in the form of raw lignocellulosic biomass. "Raw lignocellulosic biomass" refers to lignocellulosic biomass that has not been processed from its native, unaltered chemical state by any lignocellulosic pretreatments except for mechanical comminution (chopping, chipping, grinding, milling, etc.). "Lignocellulosic pretreatment," or simply "pretreatment," is a term well understood in the art that encompasses a number of treatments that change the physical and/or chemical structure of lignocellulosic biomass for downstream treatments, such as lignin depolymerization, cellulose hydrolysis, or other treatments. For descriptions of various pretreatments, see Kumar et al. 2017 and Kumar et al. 2009.

Types of lignocellulosic pretreatments include physical pretreatments, chemical pretreatments, physicochemical pretreatments, and biological pretreatments. Physical pretreatments include mechanical comminution (e.g., chipping, grinding, milling), microwave irradiation, ultrasound sonication, pyrolysis, and pulsed-electric field treatment. Chemical pretreatments include acid treatment (e.g., sulfuric acid treatment, dicarboxylic acid treatment) alkali treatment, ozonolysis, organosols treatment, ionic liquid treatment, deep eutectic solvent treatment, and natural deep eutectic solvent treatment. Physicochemical pretreatments include steam explosion, liquid hot water treatment, wet oxidation, SPORL (sulfite pretreatment to overcome recalcitrance of lignocellulose) pretreatment, ammonia-based pretreatment (e.g., ammonia fiber explosion (AFEX), ammonia recycle percolation (ARP), soaking aqueous ammonia (SAA), $CO_2$ explosion, and oxidative pretreatment. Biological pretreatments include fungi treatment (e.g., brown-rot fungi treatment, white-rot fungi treatment, soft-rot fungi treatment), bacterial treatment, archaeal treatment, and enzyme treatment (e.g., peroxidase enzyme treatment, laccase enzyme treatment). Merely washing lignocellulosic biomass with non-chemically reactive solvents such as organic solvents (e.g., dioxane) or water at a temperature under about 100° C. and a pressure at or near atmospheric does not constitute a lignocellulosic pretreatment. Organosols methods, for example, typically employ temperatures above 140° C. and elevated pressures.

In some versions of the invention, the lignocellulosic biomass can be in the form of lignocellulosic biomass that has not been treated with physical pretreatment. In some versions of the invention, the lignocellulosic biomass can be in the form of lignocellulosic biomass that has not been treated with chemical pretreatment. In some versions of the invention, the lignocellulosic biomass can be in the form of lignocellulosic biomass that has not been treated with physicochemical pretreatment. In some versions of the invention, the lignocellulosic biomass can be in the form of lignocellulosic biomass that has not been treated with biological pretreatment. In some versions of the invention, the lignocellulosic biomass can be in the form of lignocellulosic biomass that has not been treated with mechanical comminution (e.g., chipping, grinding, milling). In some versions of the invention, the lignocellulosic biomass can be in the form of lignocellulosic biomass that has not been treated with microwave irradiation. In some versions of the invention, the lignocellulosic biomass can be in the form of lignocellulosic biomass that has not been treated with ultrasound sonication. In some versions of the invention, the lignocellulosic biomass can be in the form of lignocellulosic biomass that has not been treated with pyrolysis. In some versions of the invention, the lignocellulosic biomass can be in the form of lignocellulosic biomass that has not been treated with pulsed-electric field treatment. In some versions of the invention, the lignocellulosic biomass can be in the form of lignocellulosic biomass that has not been treated with acid treatment (e.g., sulfuric acid treatment, dicarboxylic acid treatment). In some versions of the invention, the lignocellulosic biomass can be in the form of lignocellulosic biomass that has not been treated with alkali treatment. In some versions of the invention, the lignocellulosic biomass can be in the form of lignocellulosic biomass that has not been treated with ozonolysis. In some versions of the invention, the lignocellulosic biomass can be in the form of lignocellulosic biomass that has not been treated with organosols treatment. In some versions of the invention, the lignocellulosic biomass can be in the form of lignocellulosic biomass that has not been treated with ionic liquid treatment. In some versions of the invention, the lignocellulosic biomass can be in the form of lignocellulosic biomass that has not been treated with deep eutectic solvent treatment. In some versions of the invention, the lignocellulosic biomass can be in the form of lignocellulosic biomass that has not been treated with natural deep eutectic solvent treatment. In some versions of the invention, the lignocellulosic biomass can be in the form of lignocellulosic biomass that has not been treated with steam explosion. In some versions of the invention, the lignocellulosic biomass can be in the form of lignocellulosic biomass that has not been treated with liquid hot water treatment. In some versions of the invention, the lignocellulosic biomass can be in the form of lignocellulosic biomass that has not been treated with wet oxidation. In some versions of the invention, the lignocellulosic biomass can be in the form of lignocellulosic biomass that has not been treated with SPORL (sulfite pretreatment to overcome recalcitrance of lignocellulose) pretreatment. In some versions of the invention, the lignocellulosic biomass can be in the form of lignocellulosic biomass that has not been treated with ammonia-based pretreatment. In some versions of the invention, the lignocellulosic biomass can be in the form of lignocellulosic biomass that has not been treated with ammonia fiber explosion (AFEX). In some versions of the invention, the lignocellulosic biomass can be in the form of lignocellulosic biomass that has not been treated with ammonia recycle percolation (ARP). In some versions of the invention, the lignocellulosic biomass can be in the form of lignocellulosic biomass that has not been treated with soaking aqueous ammonia (SAA) treatment. In some versions of the invention, the lignocellulosic biomass can be in the form of lignocellulosic biomass that has not been treated with $CO_2$ explosion. In some versions of the invention, the lignocellulosic biomass can be in the form of lignocellulosic biomass that has not been treated with oxidative pretreatment. In some versions of the invention, the lignocellulosic biomass can be in the form of lignocellulosic biomass that has not been treated with fungi treatment. In some versions of the invention, the lignocellulosic biomass can be in the form of lignocellulosic biomass that has not been treated with brown-rot fungi treatment. In some versions of the invention, the lignocellulosic biomass can be in the form of lignocellulosic biomass that has not been treated with white-rot fungi treatment. In some versions of the invention, the lignocellulosic biomass can be in the form of lignocellulosic biomass that has not been treated with soft-rot fungi treatment. In some versions of the invention, the lignocellulosic biomass can be in the form of lignocellulosic biomass that has not been treated with bacterial treatment. In some versions of the invention, the lignocellulosic biomass can be in the form of lignocellulosic biomass that has not been treated with archaeal treatment. In some versions of the invention, the lignocellulosic biomass can be in the form of lignocellulosic biomass that has not been treated with enzyme treatment. In some versions of the invention, the lignocellulosic biomass can be in the form of lignocellulosic biomass that has not been treated with peroxidase enzyme treatment. In some versions of the invention, the lignocellulosic biomass can be in the form of lignocellulosic biomass that has not been treated with laccase enzyme treatment.

The lignocellulosic biomass can be derived from any source, such as corn cobs, corn stover, cotton seed hairs, grasses, hardwood stems, leaves, newspaper, nut shells, paper, softwood stems, switchgrass, waste papers from chemical pulps, wheat straw, wood, woody residues, and other sources.

The lignocellulosic biomass in some versions can be included in the solvent in an amount from about 0.01% w/v, about 0.05% w/v, about 0.1% w/v, about 1% w/v, about 5% w/v, about 10% w/v, or about 25% w/v to about 1% w/v, about 5% w/v, about 10% w/v, about 25% w/v, or about 50% w/v, or more.

The reacting in some versions can be conducted at a pressure from about 1 bar, about 5 bar, about 10 bar, about 20 bar, about 25 bar, about 30 bar, about 40 bar, about 45 bar, about 50 bar, or about 75 bar to about 5 bar, about 10 bar, about 20 bar, about 25 bar, about 30 bar, about 40 bar, about 45 bar, about 50 bar, about 75 bar, about 100 bar, or more.

The reacting in some versions can be conducted for a time from about 0.5 hours, about 1 hours, about 3 hours, about 10 hours to about 1 hour, about 3 hours, about 10 hours, about 30 hours, or more. The reacting is preferably conducted for a time from about 4 hours to about 16 hours, such as from about 6 hours to about 14 hours, or about 12 hours.

Figure 13A:
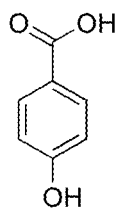
FIGS. 13A-13V. Exemplary phenolic and benzoquinone monomers shown or predicted to be produced with the methods of the invention.
Figure 13B:
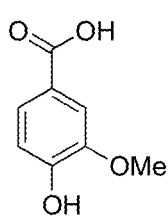
Figure 13C:
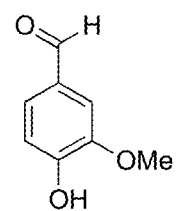
Figure 13D:
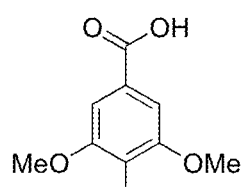
Figure 13E:
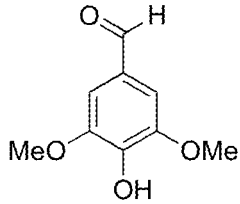
Figure 13F:
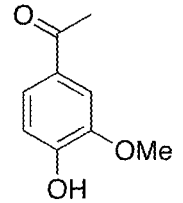
Figure 13G:
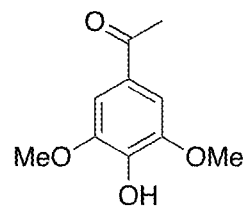
Figure 13H:
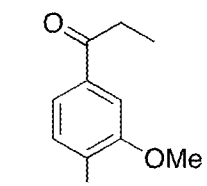
Figure 13I:
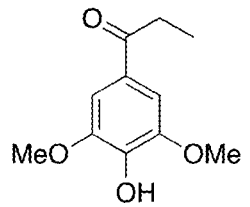
Figure 13J:
Figure 13K:
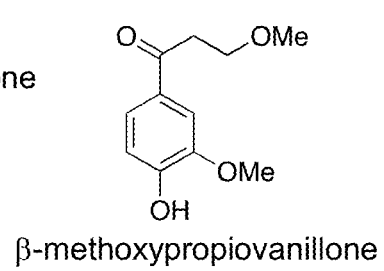
Figure 13L:
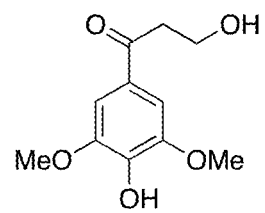
Figure 13M:
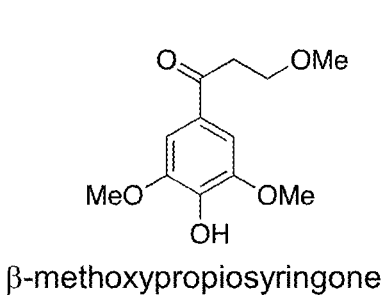
Figure 13N:
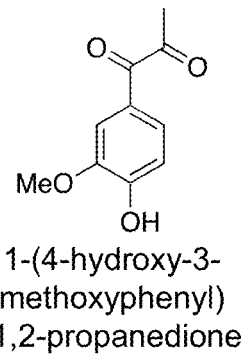
Figure 13O:
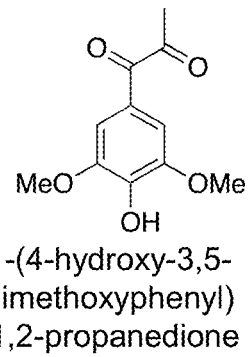
Figure 13P:
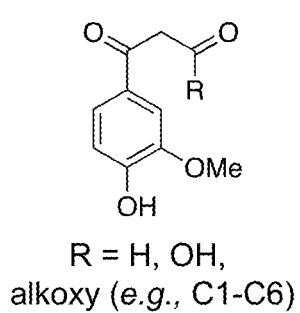
Figure 13Q:
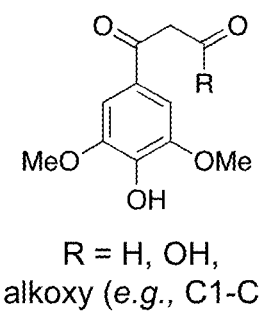
Figure 13R:
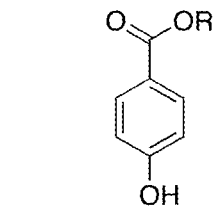
Figure 13S:
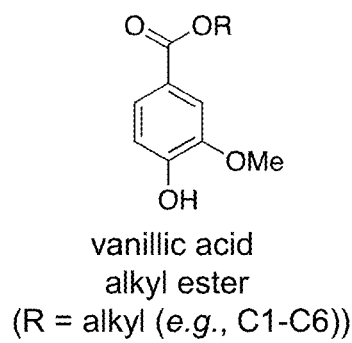
Figure 13T:
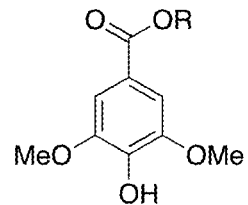
Figure 13U:
Figure 13V:
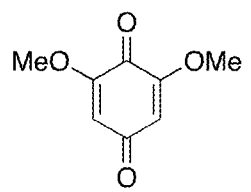

The reacting can be conducted for a time sufficient to produce one or more phenolic or benzoquinone monomers as a product. "Phenolic monomers" refers to compounds having one and only one phenolic group. The phenolic groups in the phenolic monomers can comprise p-hydroxyphenyl (H), guaiacyl (G), and/or syringyl (S) phenolic groups. The phenolic monomer products can comprise oxidized phenolic monomer products. The phenolic monomer products can comprise phenolic monomer products comprising a benzylic carbonyl. The term "benzylic" is used to describe the position of the first carbon bonded to a benzene, phenol, or other aromatic ring. Exemplary phenolic monomer products comprising a benzylic carbonyl include each of the compounds shown in FIGS. 13A-13V except for 2,6-dimethoxybenzoquinone.

The reacting can be conducted for a time sufficient to produce p-hydroxybenzoic acid at a yield of the lignin of at least about 4% w/w, at least about 5% w/w, at least about 6% w/w, at least about 7% w/w, at least about 8% w/w, or at least about 9% w/w. The reacting can be conducted for a time sufficient to produce vanillic acid at a yield of the lignin of at least about 4% w/w, at least about 5% w/w, at least about 6% w/w, at least about 7% w/w, at least about 8% w/w, at least about 9% w/w, or at least about 10% w/w. The reacting can be conducted for a time sufficient to produce syringic acid at a yield of the lignin of at least about 4% w/w, at least about 5% w/w, at least about 6% w/w, at least about 7% w/w, at least about 8% w/w, at least about 9% w/w, at least about 10% w/w, or at least about 11% w/w. The reacting can be conducted for a time sufficient to produce vanillin at a yield of the lignin of at least about 1% w/w or at least about 1.5% w/w, or at least about 2% w/w. The reacting can be conducted for a time sufficient to produce syringaldehyde at a yield of the lignin of at least about 1% w/w, at least about 1.5% w/w, at least about 2% w/w, at least about 2.5% w/w, at least about 3% w/w, at least about 3.5% w/w, at least about 4% w/w, or at least about 4.5% w/w.

Alkyl esters of p-hydroxybenzoic acid, vanillic acid, and syringic acid (FIG. 4C) can be produced by conducting the reaction in the presence of an alcoholic solvent, such as methanol, ethanol, etc. β-methoxypropiovanillone and β-methoxypropiosyringone can arise from solvolylsis of β-hydroxypropiovanillone and β-hydroxypropiosyringone, respectively.

The methods of the invention can further comprise, after the reacting, separating a carbohydrate residue from the solvent. The solvent in this step can comprise a phenolic monomer product and/or a benzoquinone monomer product therein, such that the phenolic monomer product and/or the benzoquinone monomer is separated from the carbohydrate residue in the solvent. The separating can comprise filtration, among other separation methods.

The methods of the invention can further comprise, after the reacting, isolating one or more of the catalyst, a phenolic monomer product, or a benzoquinone monomer product from the solvent. The isolating can comprise evaporating the solvent, among other isolation methods.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Oxidative Catalytic Fractionation of Raw Biomass Under Non-Alkaline Conditions

Summary

Economically viable biorefineries will depend on valorization of both sugar and lignin fractions in biomass. Pretreatment methods are commonly used to modify different components in biomass before the conversion into target products, but they often lead to chemical modification, degradation, and/or low yields of lignin. Catalytic fractionation approaches provide a possible solution to these challenges by separating the polymeric sugar and lignin fractions in the presence of a catalyst that promotes hydrogenolytic cleavage of the lignin into alkylated phenols. Here, we demonstrate an oxidative fractionation method that is conducted in the presence of a non-precious-metal Co—N/C catalyst and $O_2$. This process affords a 24 wt % yield of oxygenated aromatics from lignin while preserving a high-quality carbohydrate stream. The aromatic carboxylic acids and aldehydes derived from this process offer advantages relative to the previously reported reduction products, for example, in polymer synthesis and/or biological funneling to value-added products.

Introduction

Figure 2A:
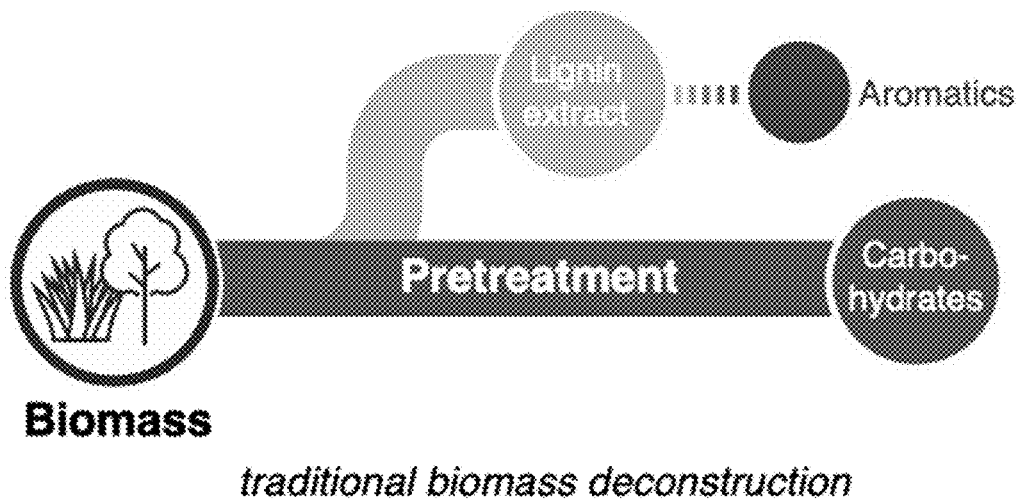
FIGS. 2A-2D. Overview of biomass deconstruction approaches.

Lignocellulosic biomass is an important renewable feedstock for the production of transportation fuels and valuable chemicals that could reduce reliance on fossil-based resources (Tuck et al. 2012, Langholtz et al. 2016). Historical efforts on biomass conversion, ranging from the pulp and paper industry to more recent efforts on bioethanol production, have emphasized utilization of carbohydrates. Although these polymeric sugars represent the major fraction (70-85 wt %) of nonedible biomass (McKendry et al. 2002, Mosier et al. 2005), there is growing recognition that valorization of lignin will be crucial to the economic viability of biorefineries (Ragauskas et al. 2014, Li et al. 2015, Sun et al. 2018, Schutyser and Renders et al. 2018). Lignin is a structurally complex heterogeneous aromatic biopolymer that represents the largest renewable source of aromatic chemicals. Conventional lignocellulosic biomass conversion methods for the isolation of carbohydrates, however, often result in chemical modification or degradation of the lignin (FIG. 2A). Although the lignin extracted from these processes has found some direct commercial application (Lora 2008, Strassberger et al. 2014), it is commonly burned for energy production and it is not well suited for large-scale conversion into aromatic chemicals. The challenges in lignin isolation often arise from side-reactions initiated by benzyl alcohols present in the lignin backbone between the aromatic subunits (Rinaldi et al. 2016, Renders et al. 2017). Under acidic conditions, facile generation of carbocation intermediates, and under alkaline conditions, the formation of quinone methide and/or epoxides at these sites can lead to polymer cross-linking resulting in the formation of recalcitrant C—C bonds that prevent conversion of lignin into aromatic monomers.

Figure 2B:
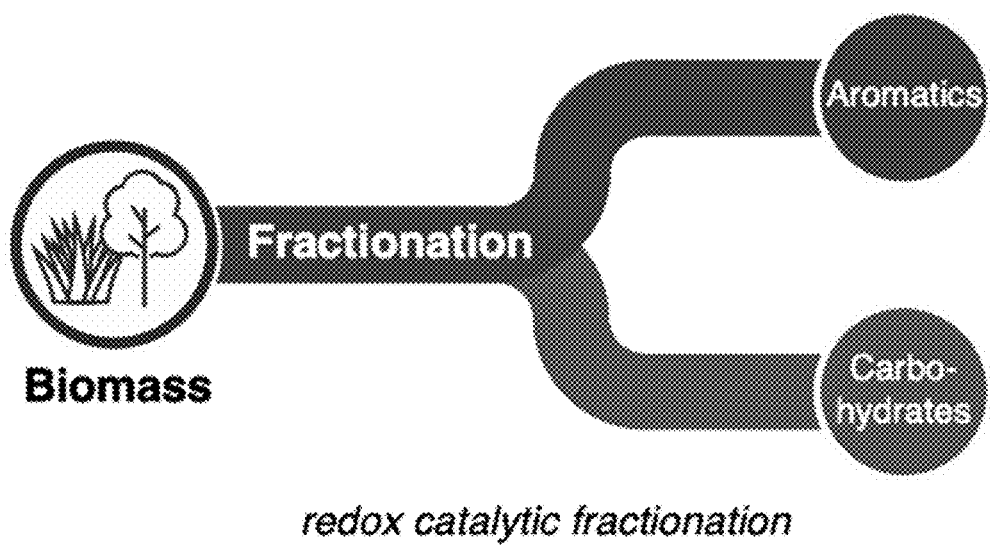
Figure 2C:
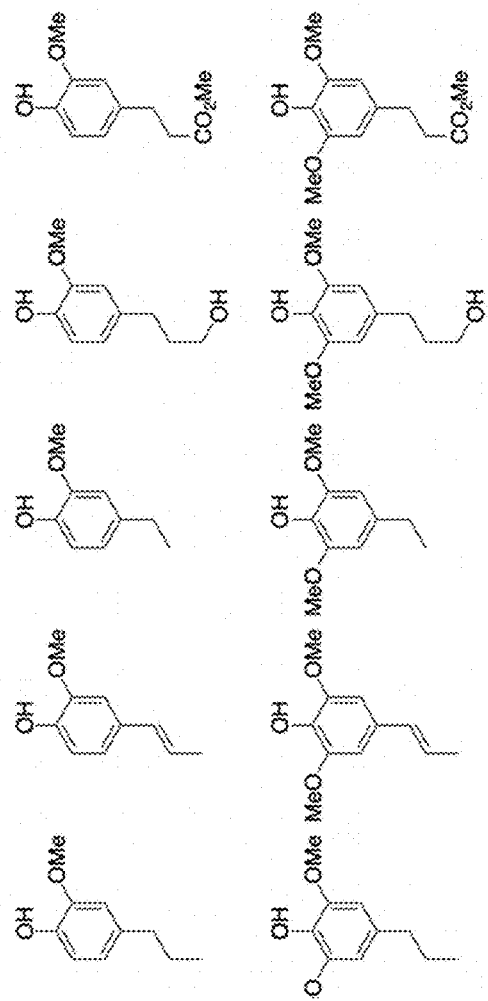

The issues noted above have contributed to growing interest in "reductive catalytic fractionation" methods (Rinaldi et al. 2016, Renders et al. 2019), a biomass pretreatment strategy in which separation of the carbohydrate and lignin fractions takes place in the presence of a heterogeneous catalyst and source of $H_2$ (hydrogen gas, formic acid or alcohol solvent). As the lignin dissolves, it is converted directly into aromatic monomers via catalytic hydrogenolysis (FIG. 2B), thereby avoiding the degradation pathways that occur during conventional pretreatment methods. The products are primarily syringyl- and guaiacyl-derived phenols bearing (partially) deoxygenated hydrocarbon substituents (FIG. 2C), with specific compositions varying with the catalyst (e.g., Pd/C, Ru/C, Ni/C), reaction conditions, and source of biomass (Li et al. 2012, Song et al. 2013, Klein et al. 2016, Luo et al. 2016, Huang et al. 2017, Van den Bosch et al. 2017, Anderson et al. 2017, Kumaniaev et al. 2017, Anderson et al. 2018). These compounds are being explored as precursors to fuels and fuel additives (Sun et al. 2018), monomers for polymeric materials (Koelewijn et al. 2018, Wang et al. 2018), and fine chemicals (Parsell et al. 2015, Elangovan et al. 2019).

Figure 2D:
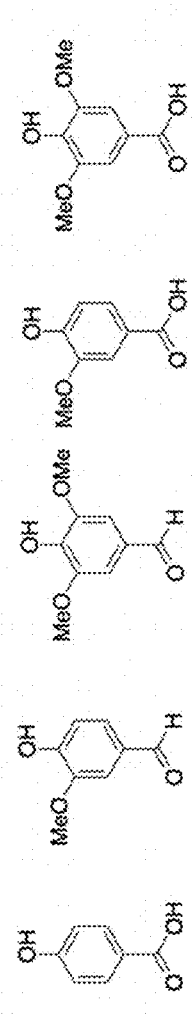

The present examples show oxidative catalytic fractionation (OCF) as a means to access lignin-derived products (FIG. 2D) different from those obtained under reductive catalytic fractionation conditions. The prospective oxidized bifunctional compounds in FIG. 2D offer potential advantages as monomers for the synthesis of bio-based polymers (Llevo et al. 2016). In addition, they represent appealing alternatives to reduced products as feedstocks for microbial conversion and biological funneling, due their increased water solubility and similarity (or identity) to known metabolic intermediates (Beckham et al. 2016, Perez et al. 2019). The oxidation of lignin derived from conventional pretreatment methods (cf. FIG. 2A) and lignin model compounds has been studied extensively (Ma et al. 2015, Behling et al. 2016, Vangeel et al. 2018, Rahimi et al. 2013, Rahimi et al. 2014, Lancefield et al. 2015, Bosque et al. 2017, Das et al. 2018, Rafiee et al. 2019, Song et al. 2018). We speculated that pretreatment of biomass in the presence of a suitable catalyst and $O_2$ could provide the basis for an oxidative catalytic fraction method analogous to reductive catalytic fractionation but capable of generating oxidized aromatic products in combination with a carbohydrate fraction. Previous biomass processing methods have employed alkaline aqueous conditions with a number of different catalysts (Tarabanko and Kaygorodov al. 2017, Schutyser and Kruger et al. 2018), but the simultaneous production of good yields of oxidized aromatic monomers and high-quality cellulose has proven to be difficult. The present examples employ non-basic conditions in organic solvent that allow for simultaneous production of oxidizes aromatic chemicals from lignin and a high-quality carbohydrate stream.

Methods

General Considerations

All reagents were purchased and used as received without further purification unless otherwise noted. Acetone, acetonitrile, 1,4-dioxane, dimethyl carbonate, ethyl acetate, aniline, ammonium peroxydisulfate, $Co(OAc)_2 \cdot 4H_2O$, $Co(NO_3)_2 \cdot 6H_2O$, $Fe(NO_3)_2 \cdot 6H_2O$, $FeCl_3 \cdot 6H_2O$, $Co_3O_4$, $Fe_2O_3$, $MnO$, $CuO$, $CeO_2$, Pd/C (5 wt % metal loading), Pt/C (5 wt % metal loading), Ru/C (5 wt % metal loading), DARCO KB-G active charcoal were purchased from Sigma Aldrich. $TiO_2$ was purchased from Eastman Fine Chemicals. Methanol was purchased from Fisher Scientific. Ethanol was purchased from Pharmco-Aaper. Phenanthroline was purchased from Oakwood Chemical. Carbon black (VXC72R) was purchased from Cabot Chemical. NE-19 poplar was obtained from the Great Lakes Bioenergy Research Center in Madison, WI. The poplar was ground to a particle size of 20 mesh and washed in a Soxhlet extractor with subsequent 24-hour ethanol, toluene, 1,4 dioxane washes. Wiley milled (1 mm) lodgepole pine and birch samples were obtained from the USDA Forest Products Laboratory in Madison, WI. The miscanthus sample obtained from the Great Lakes Bioenergy Research Center in Madison, WI, and was ground to 5 mm.

Solid state NMR (ssNMR) spectra were obtained with Bruker Avance 111-500 MHz NMR spectrometer with a Doty 4 mm $^1$H/X/Y DSI MAS probe and Bruker MAS III controller unit. All samples were packed into thin-walled, 4 mm silicon nitride rotors with Kel-F caps. A standard cross polarization pulse sequence was used with the acquisition parameters listed in Table 1. Chemical shifts are reported in parts per million (ppm).

TABLE 1

| Solid state NMR spectra acquisition parameters. | |
|---|---|
| Number of scans | 5358 |
| Sweep width (ppm) | 496.848 |
| Acquisition time (s) | 0.029936 |
| Receiver gain | 201.52 |
| O1 ($^1$H in PPM) | 4.7 |
| O1 ($^{13}$C in PPM) | 100 |
| Sample spinning rate (Hz) | 10,000 |
| Probe temperature (K) | 297.2 |

Figure 3A:
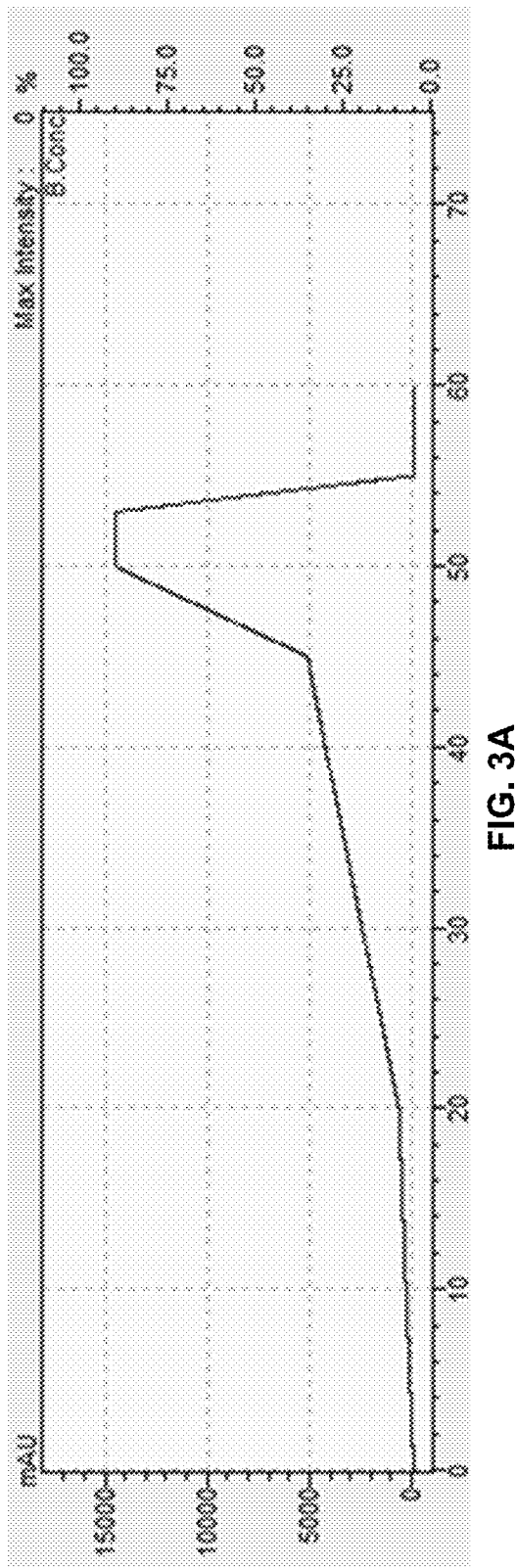
FIGS. 3A and 3B. HPLC programs.
Figure 3B:
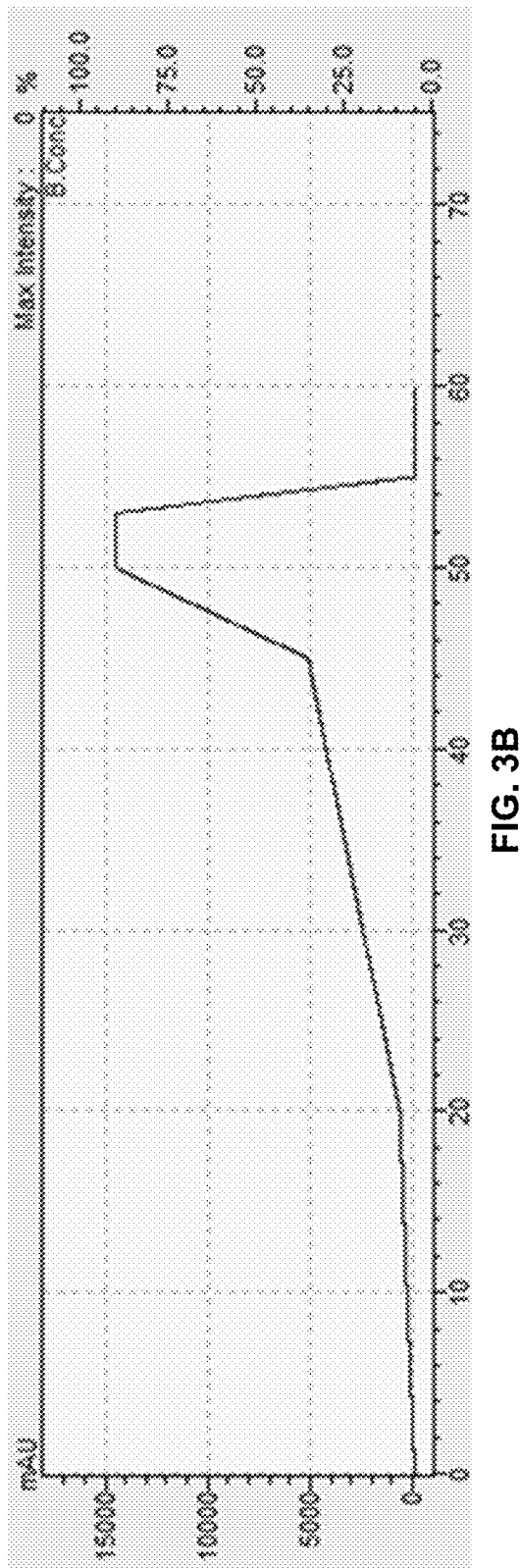

HPLC/UV analysis on lignin-derived monomers and oligomers was obtained on a Shimadzu Prominence HPLC system equipped with a SPD-M20A diode array detector and a Restek Ultra C18 column (150 mm×4.6 mm ID—3 micron particle size) at 35° C. Solvent A was 0.1% formic acid in Millipure water and solvent B was acetonitrile for the HPLC separations. Monomer yields were calculated based on a 1,4-dimethoxybenzene internal standard. The gradient of solvent B (acetonitrile) is shown in FIG. 3A. Semipreparative scale isolations of the lignin oligomers was done using a Restek Ultra C18 column (100 mm×21.2 mm ID—5-micron particle size) at 35° C. The gradient profile for collecting the oligomers is shown in FIG. 3B.

Xylose and glucose were quantified by HPLC analysis using an Agilent 1260 Infinity HPLC system with an RID detector equipped with a Biorad Aminex HPX-87H column (300×7.8 mm) and Cation-H guard column. The mobile phase was 0.02 N $H_2SO_4$, with a flow rate of 0.500 mL/min and a column temperature of 50° C. Reference standards were used to quantify the glucose and xylose concentrations.

Gel permeation chromatography (GPC) characterization of lignin-derived oligomers was conducted using a PSS PolarSil Linear S column with solution of 0.1 M lithium bromide (LiBr) in dimethyl formamide (DMF) as the mobile phase (flow rate of 0.3 mL/min). The sample concentrations were 1 mg/ml (dissolved in same solution as mobile phase) and the samples were sonicated for 1 h and filtered through a 0.2 um PTFE membrane prior to analysis.

A modified version of NREL/TP-510-42618 (Sluiter et al. 2012) was used to quantify the glucan, xylan, and lignin amounts in the NE-19 poplar, as well as the lignin quantities in the pine, miscanthus, and birch samples.

Special caution should be used when handling reactions performed in organic solvents at elevated temperature under oxygen atmosphere (Osterberg 2015). Oxygen diluted with an inert gas, such as $N_2$ or Ar, should be used to stay below the limiting oxygen concentration (LOC) of the organic solvent to prevent combustion.

Oxidative Depolymerization of Lignin in Raw Biomass

In a typical lignin depolymerization reaction of poplar, 0.1 g washed NE-19 poplar species, 10 wt % (determined relative to the biomass substrate (e.g., poplar, etc.)) of a heterogeneous catalyst, and 25 mL solvent were added to a Hastelloy steel Parr reactor. A microporous cage (40-micron pores) was used to separate the heterogeneous catalyst and the biomass/carbohydrates. The catalyst cage had the functionality to allow solvent as well as soluble solute to pass through and access the catalyst, while at the same time keep biomass substrate separate from the catalyst. This cage was attached to the vessel head. Following addition of biomass, solvent, catalyst, and a Teflon stir bar, the pressure vessel was sealed. The system was first purged with 6% $O_2$ (balanced by $N_2$) 3 times while stirring, and then the system was pressurized with 35 bar 6% $O_2$. The mixture was then heated at 190° C. for 12 h. After 12 h, the heating was stopped, and the mixture was allowed to cool to room temperature. The system was vented, and the pressure head and catalyst cage were removed. The reaction mixture was filtered to separate the liquid phase containing the aromatic products from the solid biomass residue. The residue was washed with additional acetone to remove the remaining phenolic products from the surface, and the resulting solution was combined with the filtrate. The combined liquid phase was condensed by rotary evaporation, diluted in a volumetric flask (5 mL), and then analyzed by HPLC/UV. The solid biomass residue was left to dry thoroughly under ambient conditions.

Metal on Nitrogen-Doped Carbon (M-N/C) Catalyst Preparation

Co-PANI/C and Fe-PANI/C catalysts were prepared according to previous published report (Wu et al. 2011). Specifically, 2 g of carbon support (carbon black, either VXC72R from Cabot Chemical or DARCO KB-G activated carbon from Sigma Aldrich) was first treated in 45 mL concentrated $HNO_3$ solution at room temperature for 48 hours to remove surface impurities. The carbon supported was then filtered under vacuum followed by drying in a vacuum oven overnight. 2.0 mL aniline was then added to 0.4 g of acid treated carbon support in 15 mL 0.5 N HCl solution. The suspension was stirred in ice bath while for ten minutes before metal precursors and the oxidant (ammonium peroxydisulfate, APS, 4.4 g) were added. $Co(NO_3)_2 \cdot 6H_2O$ (1.024 g) and $FeCl_3 \cdot 6H_2O$ (0.570 g added in two portions) were used as precursors for Co-PANIC and Fe-PANI/C catalysts, respectively. After stirring for 24 hours, the suspension was filtered and the recovered solid was dried under vacuum. A first pyrolysis was performed at 850° C. for 1 hour in an inert nitrogen atmosphere in a vertical Carbolite Gero MTF Model 12/38 tube furnace with a 3216 temperature controller. This "heat-treated" sample was then stirred in 0.5 M $H_2SO_4$ at 80° C. for 8 hours to remove any unstable and inactive species from the catalyst, and thoroughly washed with DI water. The acid treated sample was then filtered and dried before a second pyrolysis process under a nitrogen atmosphere at 850° C. for 3 hours.

The Co-Phen/C catalyst was prepared in a similar previously reported method (Jagadeesh et al. 2013). 508 mg of $Co(OAc)_2 \cdot 4H_2O$, 720 mg of phenanthroline and 2.7 g of acid-treated carbon support (same treatment as above) was added to 50 mL of ethanol. After stirring for 24 hours at room temperature, the suspension was filtered and the recovered solid was vacuum-dried. The sample was pyrolyzed at 800° C. for 2 hours in under inert nitrogen atmosphere.

Quantification of lignin-, glucan-, and xylan-Derived Products

To fully characterize the reaction products post-oxidative catalytic fractionation treatment, both the solid residue and the liquid phase were analyzed further.

Solid residue: The solid residue obtained after filtration was air dried and weighed. The mass of the residue was 55.2 mg. A modified version of NREL/TP-510-42618 was used to quantify the glucans and xylans present in the solid residue. After acid hydrolysis, HPLC analysis showed that the residue composition consisted of 71.5% glucose and 8.1% xylose. These results correlate to 39.5 mg of glucans and 4.5 mg of xylans in the solid residue, accounting for 83% and 32% of the material from the raw biomass, respectively.

Liquid fraction: After solvent removal, the dried sample was dissolved in ethyl acetate and extracted with water. The aqueous phase was separated and dried. The solids from the aqueous extraction were hydrolyzed with 72 wt % sulfuric acid at 30° C. for one hour, diluted to a sulfuric acid concentration of 4%, and heated at 120° C. for one hour. The resultant solution was analyzed by HPLC to quantify the xylose and glucose. The results indicated that 1.3 mg of xylose and 0.8 mg glucose were present in this aqueous fraction, corresponding to 9.4% and 1.7% of the xylans and glucans in the raw biomass, respectively. The ethyl acetate layer was analyzed by HPLC to quantify the monomers, and the results correspond to 5.0 mg of monomers, correlating to a 24% yield relative to the lignin in the raw biomass. The oligomers were separated using prep-HPLC and dried. The mass of oligomers was 12.1 mg, corresponding to 62% of the mass of the original lignin.

Overall, 85% of the lignin, 84% of the glucans, and 41% of the xylans were accounted for after oxidative catalytic fractionation processing of raw poplar biomass.

Results and Discussion

Overview of Strategy and Reaction Components

We envisioned that oxidation of biomass could take place in an organic solvent capable of promoting solvolytic separation of lignin from the carbohydrates under an atmosphere of oxygen gas. In an ideal scenario, the lignin will dissolve into solution and be susceptible to oxidation-initiated depolymerization and the carbohydrates will remain as a solid, thereby protecting them from oxidative degradation. The heterogeneous catalyst for lignin oxidation/depolymerization can be integrated within a porous cage (Luo et al. 2016, Van den Bosch et al. 2017) to avoid contamination of the solid carbohydrate fraction. The pores of the cage are designed to be large enough to allow soluble lignin to enter, but small enough to prevent passage of catalyst particles into the reaction vessel. A schematic diagram of the assembled reactor and various components of the reaction mixture is shown in FIG. 4A.

Figures 4A, 4B:
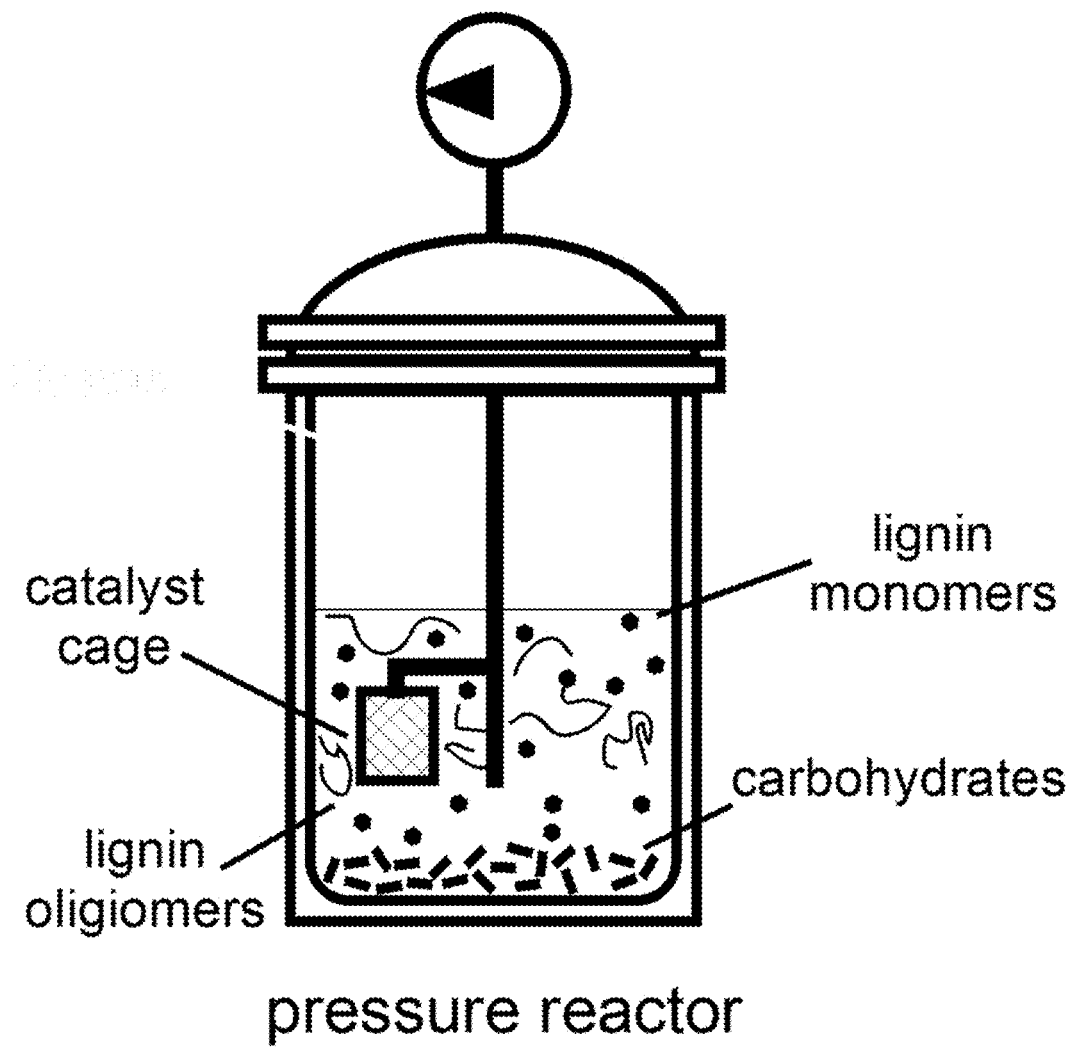
FIGS. 4A and 4B. Overview of oxidative catalytic fractionation process development.

A series of different variables were evaluated (FIG. 4B). The majority of the examples were conducted with poplar as a representative hardwood biomass source, but birch (another hardwood), pine (softwood), and miscanthus (a grass) were also evaluated. Solvents included both aprotic (acetone, acetonitrile, ethyl acetate, 1,4-dioxane, and dimethyl carbonate) and protic (methanol, ethanol, and water) examples. A range of different catalyst compositions (Tarabanko and Tarabanko 2017, Mallat et al. 2004, Sun et al. 2017, He et al. 2016, Jagadeesh et al. 2013, Preger et al. 2018, Luo and Wang et al. 2018, Liu et al. 2019) were tested, including metal oxides, supported platinum-group metals (PGMs), and metal-containing nitrogen-doped carbon catalysts (M-N/C). The M-N/C catalysts are typically prepared by adsorption of a metal salt and a source of nitrogen onto a carbon support, followed by pyrolysis under an inert atmosphere. For example, Co-PANI/C, which was identified as an effective catalyst in the examples described below, uses polyaniline (PANI) derived from in situ polymerization of aniline on the carbon support as the nitrogen source.

Biomass Oxidation and Analysis of Lignin-Derived Products

The oxidative catalytic fractionation of poplar (20 mesh) was examined under a variety of conditions by testing the parameters noted above (FIGS. 1, 2B, 4A, and 4B). Representative reaction conditions employed a 10 wt % catalyst loading with 2 bar partial pressure of $O_2$ (supplied as a gas mixture of 6% $O_2$ in $N_2$ to stay below the solvent flammability limits (Huang et al. 2017)), at 190° C. for 12 h. Following the reaction, the soluble and insoluble fractions were separated, and the soluble fraction was analyzed by HPLC to identify and quantify the low molecular weight products.

Figure 5A:
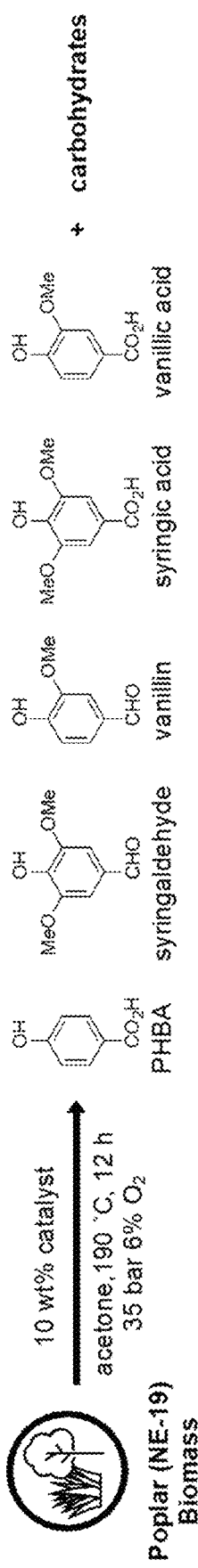
FIG. 5A. Schema of oxidative catalytic fractionation of raw poplar biomass and resulting products. Conditions: 0.1 g poplar, 10 wt % heterogeneous catalyst (e.g., Co-PANI/C), 25 mL acetone, 190° C., 35 bar 6% $O_2$ in $N_2$, 12 h.
Figure 5B:
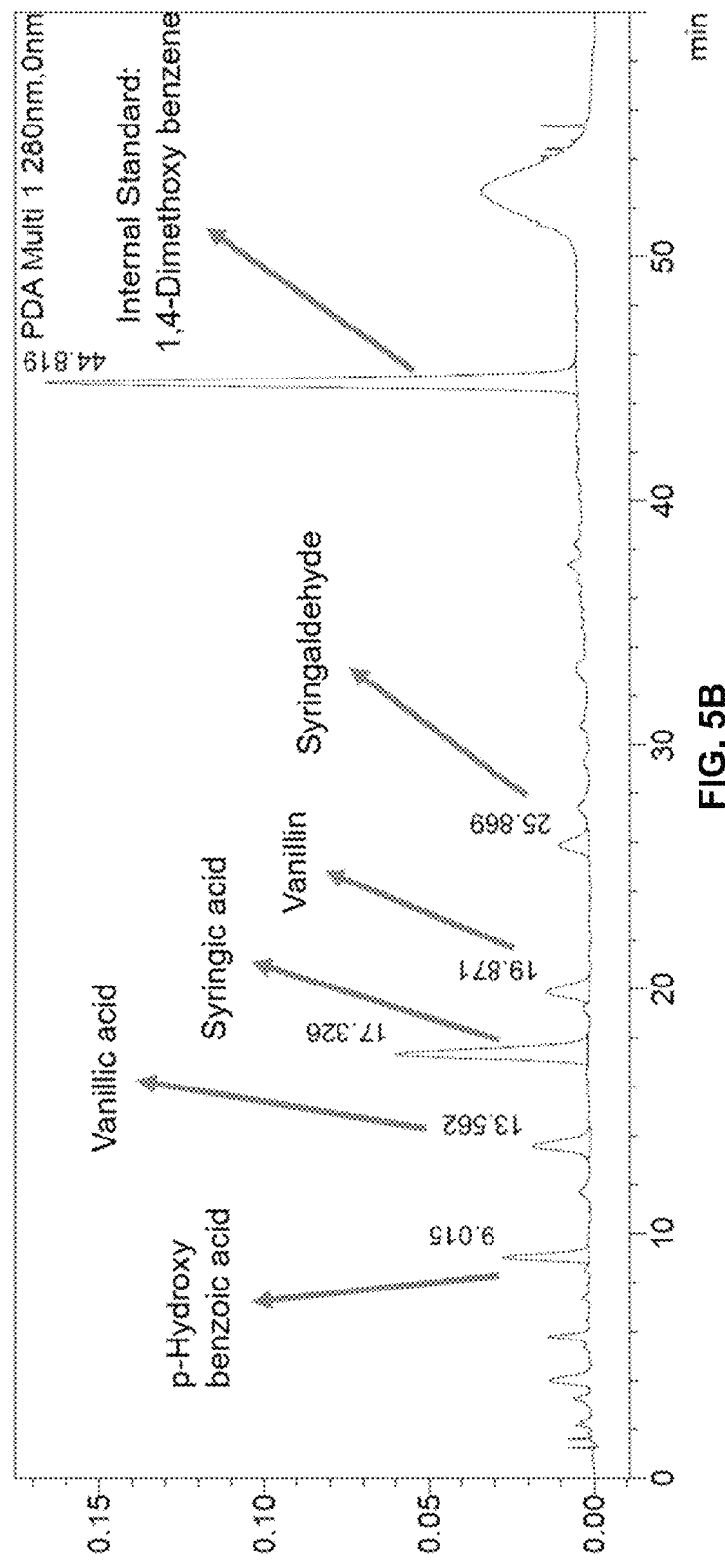
FIG. 5B. HPLC chromatogram showing identity of monomers from oxidative catalytic fractionation of poplar lignin. Monomers were detected by measuring the optical absorbance at 280 nm. The yields of monomers were quantified based on an internal standard, 1,4-dimethoxybenzene. Reaction conditions: 100 mg poplar, 10 wt % Co-PANI-C, 25 mL acetone, 190° C., 12 h, 35 bar 6% $O_2$.
Figure 8:
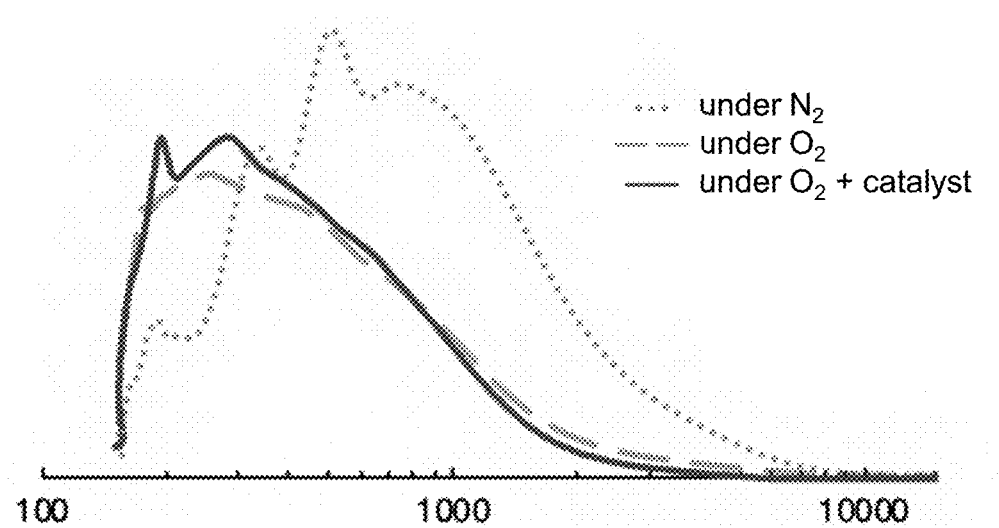
FIG. 8. GPC analysis of lignin-derived oligomers after lignin extraction under $N_2$ and $O_2$ without catalyst and under $O_2$ with Co-PANI/C. Conditions: 0.1 g poplar, 10 wt % Co-PANI/C catalyst (or absent), 25 mL solvent, 190° C., 35 bar 6% $O_2$ in $N_2$ (or only $N_2$), 12 hours.

Five aromatic compounds, including p-hydroxybenzoic acid (PHBA), vanillic acid, syringic acid, vanillin, and syringaldehyde, were identified as monomeric products of the reactions, together with a collection of higher molecular weight products (FIGS. 5A, 5B, and 8).

Figure 6:
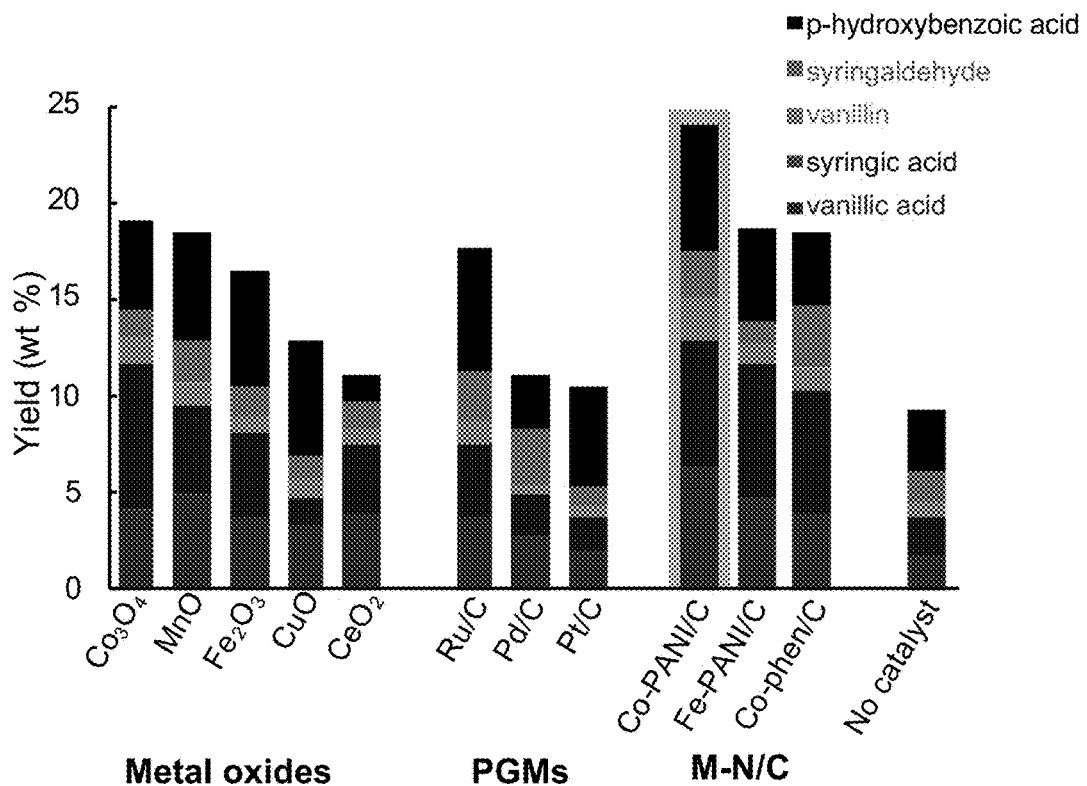
FIG. 6. Catalyst screen for the oxidative catalytic fractionation of raw poplar biomass. Conditions: 0.1 g poplar, 10 wt % heterogeneous catalyst, 25 mL acetone, 190° C., 35 bar 6% $O_2$ in $N_2$, 12 h.

Results obtained with different catalysts (FIG. 6, Table 2) revealed that Co-PANI/C (3 wt % Co) was the optimal catalyst, affording a 24.0 wt % total yield of aromatic monomers relative to the mass of lignin in the sample of biomass. Ru/C was the most effective PGM catalyst (17.6 wt % yield), but a number of non-precious metal catalysts outperformed the PGM catalysts, including $Co_3O_4$ (19.1 wt %), MnO (18.4 wt %), and all three of the M-N/C catalysts (18.5-24.0 wt %) (FIG. 6, Table 2). Treatment of poplar with $O_2$ under the optimized reaction conditions, but in the absence of catalyst, resulted in 9.2 wt % yield of monomers (FIG. 6, Table 2).

TABLE 2

Monomer yields from oxidative catalytic fractionation of raw poplar using different catalysts.[a]
Yields of major phenolic products (weight %)

| Catalyst | PHBA[b] | Vanillic acid | Syringic acid | Vanillin | Syringaldehyde | Total (wt %) |
| --- | --- | --- | --- | --- | --- | --- |
| Co-PANI-C | 6.5 | 6.2 | 6.7 | 2.0 | 2.6 | 24.0 |
| Fe-PANI-C | 4.7 | 3.1 | 6.0 | 0.6 | 3.2 | 17.6 |
| Co-Phen-C | 3.7 | 4.0 | 6.2 | 1.3 | 3.2 | 18.4 |
| $Co_3O_4$ | 4.8 | 4.2 | 7.6 | 1.3 | 1.4 | 19.3 |
| $Fe_2O_3$ | 5.9 | 4.3 | 3.2 | 0.9 | 1.6 | 15.9 |
| MnO | 5.5 | 4.8 | 4.6 | 1.3 | 2.1 | 18.3 |
| CuO | 6.1 | 3.2 | 1.4 | 0.9 | 1.2 | 12.8 |
| $CeO_2$ | 1.4 | 3.9 | 3.5 | 0.9 | 1.3 | 11.0 |
| Pd/C | 2.7 | 2.6 | 2.3 | 0.4 | 3.0 | 11.0 |
| Pt/C | 5.2 | 2.0 | 1.7 | 0.6 | 1.1 | 10.6 |
| Ru/C | 6.3 | 3.7 | 3.7 | 1.2 | 2.7 | 17.6 |
| No catalyst | 3.1 | 1.6 | 2.1 | 0.9 | 1.5 | 9.2 |

[a]Reaction conditions: 100 mg poplar, 10 wt % heterogeneous catalyst, 25 mL acetone, 190° C., 12 h, 35 bar 6% $O_2$.
[b]PHBA = para-hydroxybenzoic acid.

Figure 7:
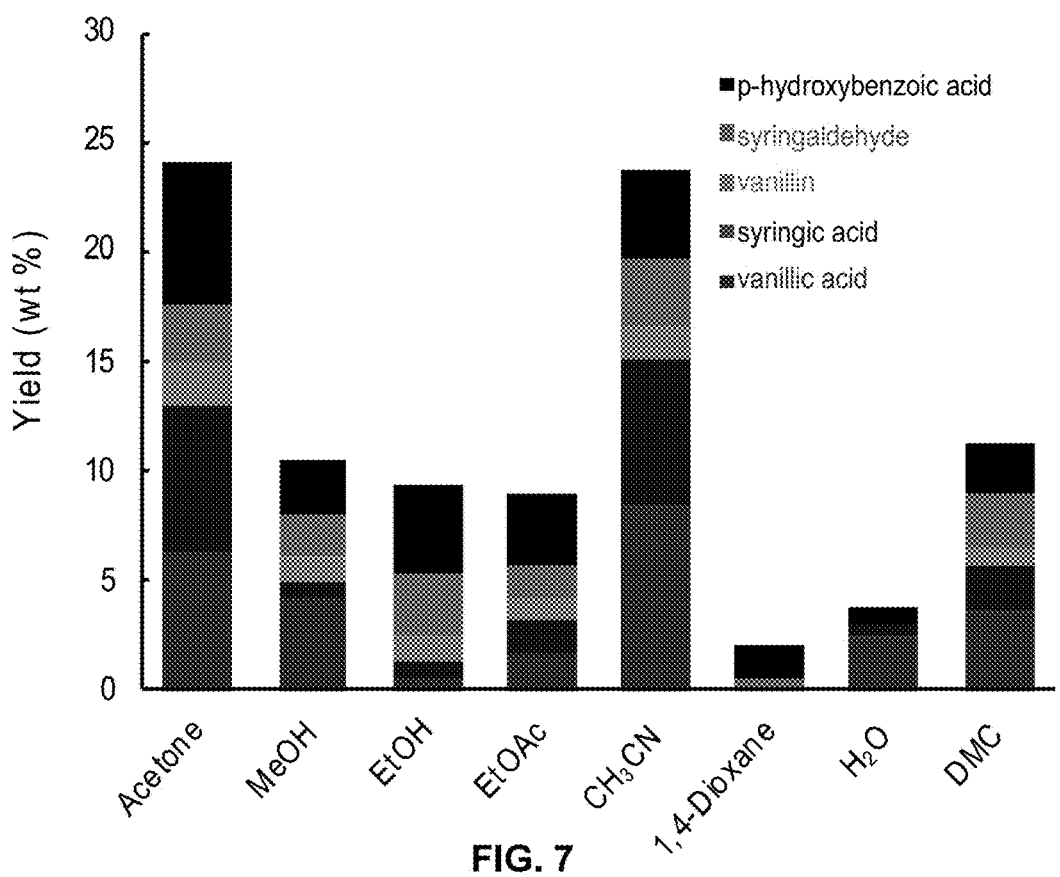
FIG. 7. Monomer yields from oxidative catalytic fractionation of raw poplar biomass using different solvents. Conditions: 0.1 g poplar, 10 wt % Co-PANI/C catalyst, 25 mL solvent, 190° C., 35 bar 6% $O_2$ in $N_2$, 12 hours.

Acetone proved to be the optimal solvent, but good monomer yields were also observed in acetonitrile (20.5 wt % monomers) (FIG. 7, Table 3).

TABLE 3

Monomer yields from oxidative catalytic fractionation of raw poplar biomass using different solvents.[a]
Yields of major phenolic products (weight %)

| Solvent | PHBA[b] | Vanillic acid | Syringic acid | Vanillin | Syringaldehyde | Total (wt %) |
| --- | --- | --- | --- | --- | --- | --- |
| Acetone | 6.5 | 6.2 | 6.7 | 2.0 | 2.6 | 24.0 |
| Methanol | 2.4 | 4.2 | 0.8 | 1.1 | 2.0 | 10.5 |
| Ethanol | 3.9 | 0.5 | 0.9 | 1.0 | 3.0 | 9.3 |
| Ethyl acetate | 3.1 | 1.7 | 1.6 | 0.8 | 1.7 | 8.9 |
| Acetonitrile | 3.9 | 8.3 | 6.7 | 1.7 | 3.0 | 23.6 |
| 1,4-Dioxane | 1.6 | 0.0 | 0.0 | 0.2 | 0.3 | 2.1 |
| $H_2O$ | 0.7 | 2.5 | 0.6 | 0.0 | 0.0 | 3.8 |
| Dimethyl carbonate | 2.3 | 3.7 | 2.0 | 0.8 | 2.4 | 11.2 |

[a]Reaction conditions: 100 mg poplar, 10 wt % Co-PANI-C catalyst, 25 mL solvent, 190° C., 12 h, 35 bar 6% $O_2$.
[b]PHBA = para-hydroxybenzoic acid.

Gel-permeation chromatography (GPC) was used to analyze the higher molecular weight products obtained from three different variations of the optimized reaction conditions: (a) the standard conditions with Co-PANI/C as the catalyst under 2 bar $O_2$ partial pressure, (b) in the absence of a catalyst, and (c) in the absence of catalyst and under anaerobic conditions (35 bar $N_2$) (FIG. 8). The higher molecular weight lignin products were separated from the monomers via semi-preparative HPLC prior to analysis of the former fraction by GPC. The material obtained from the catalyst-free anaerobic conditions exhibited a molecular weight distribution with Mw and Mn values of 775 and 386 Da, respectively. Lower molecular weight materials were obtained from the aerobic reactions, with Mw and Mn values of 455 and 256 Da from the catalyst-free conditions, and Mw and Mn values of 375 and 265 Da from the conditions with both catalyst and $O_2$. These results support that lignin depolymerization can occur purely via action of the solvent, but further depolymerization occurs under $O_2$, especially in the presence of the Co-PANI/C catalyst.

Figure 9:
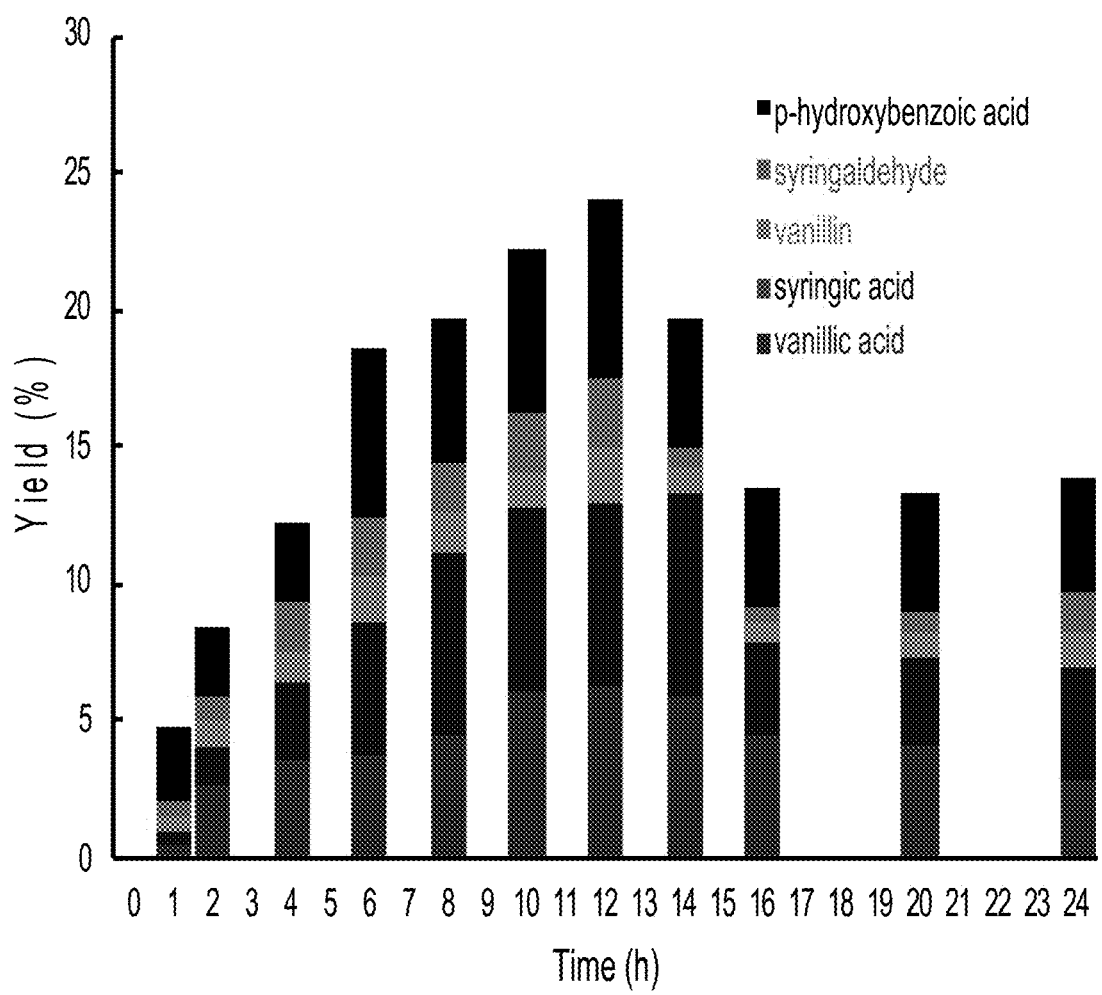
FIG. 9. Time course of monomer yields from oxidative catalytic fractionation of raw poplar. Conditions: 0.1 g poplar, 10 wt % Co-PANI/C catalyst, 25 mL solvent, 190° C., 35 bar 6% $O_2$ in $N_2$.

A time course study of the oxidative catalytic fractionation of the raw poplar was performed. Results show that monomer yields increased up to 12 hours and decreased thereafter. (FIG. 9 and Table 4).

TABLE 4

Time course study of lignin oxidative depolymerization.[a]
Yields % of major phenolic products

| Time (h) | PHBA | Vanillic Acid | Syringic Acid | Vanillin | Syringaldehyde | Total (wt %) |
|---|---|---|---|---|---|---|
| 1  | 2.6 | 0.5 | 0.5 | 0.6 | 0.5 | 4.7 |
| 2  | 2.6 | 2.7 | 1.3 | 0.9 | 0.9 | 8.4 |
| 4  | 3.0 | 3.5 | 3.0 | 1.0 | 1.8 | 12.3 |
| 6  | 6.1 | 3.7 | 4.9 | 1.6 | 2.2 | 18.5 |
| 8  | 5.2 | 4.5 | 6.6 | 1.4 | 1.9 | 19.6 |
| 10 | 6.0 | 6.0 | 6.7 | 1.4 | 2.1 | 22.2 |
| 12 | 6.5 | 6.2 | 6.7 | 2.0 | 2.6 | 24.0 |
| 14 | 4.8 | 5.9 | 7.4 | 0.9 | 0.7 | 19.7 |
| 16 | 4.3 | 4.4 | 3.4 | 0.8 | 0.5 | 13.5 |
| 20 | 4.3 | 4.0 | 3.3 | 0.9 | 0.8 | 13.3 |
| 24 | 4.3 | 2.8 | 4.2 | 1.2 | 1.4 | 13.9 |

[a]Reaction conditions: 100 mg poplar, 10 wt % heterogeneous catalyst, 25 mL acetone, 190° C., 12 h, 35 bar 6% $O_2$.
[b]PHBA = para-hydroxybenzoic acid.

Figure 10:
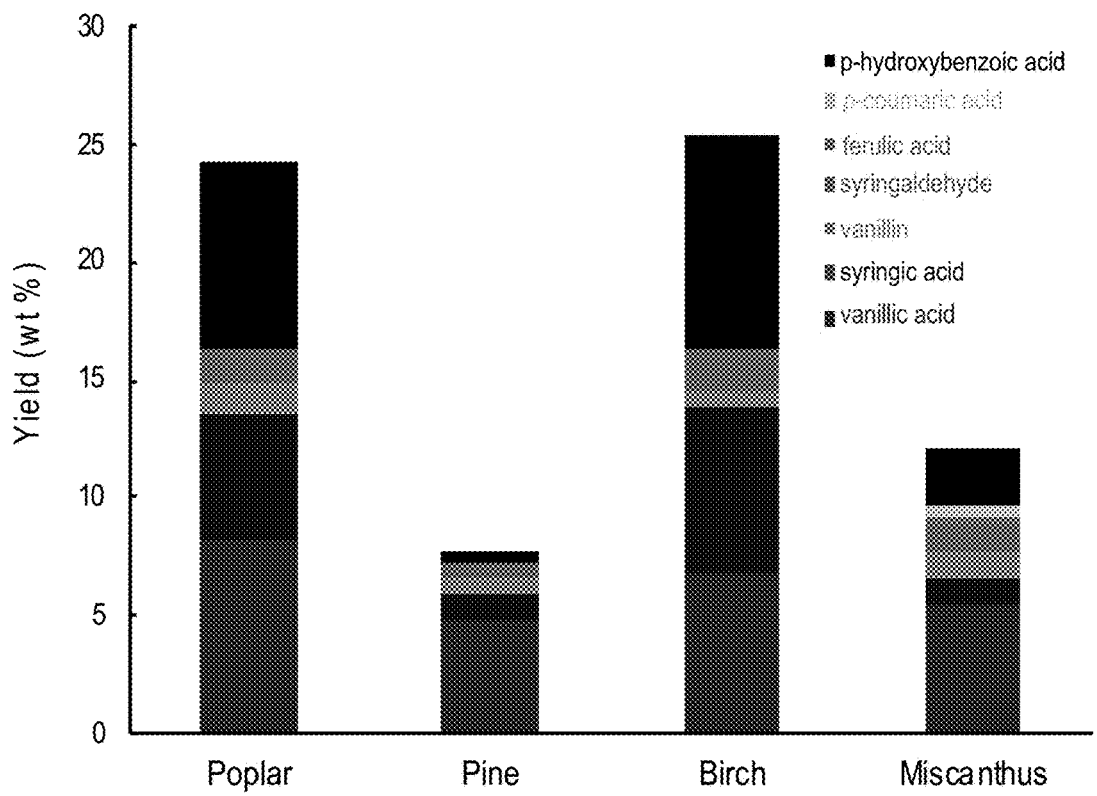
FIG. 10. Oxidative catalytic fractionation results using various biomass sources, including hardwood (poplar, birch), softwood (pine), grass (miscanthus). Conditions: 0.1 g biomass, 10 wt % Co-PANI/C, 25 mL acetone, 190° C., 35 bar 6% $O_2$ in $N_2$, 12 h.
Figure 11A:
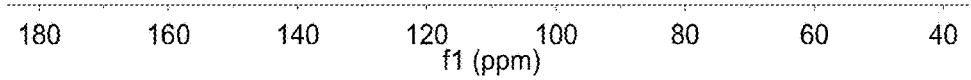
FIGS. 11A-11C. Structure characterization of raw biomass and carbohydrate residue.
Figure 11B:
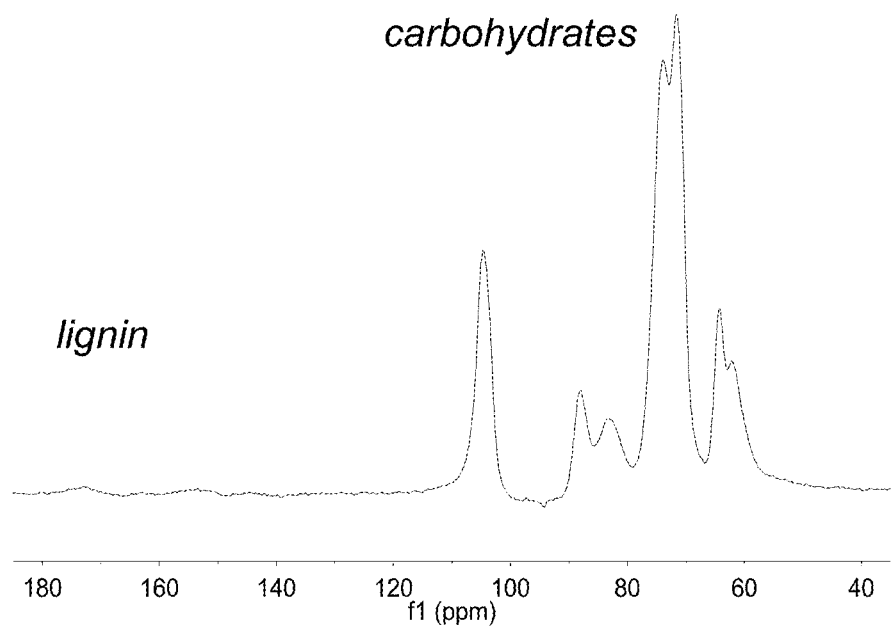
Figure 11C:
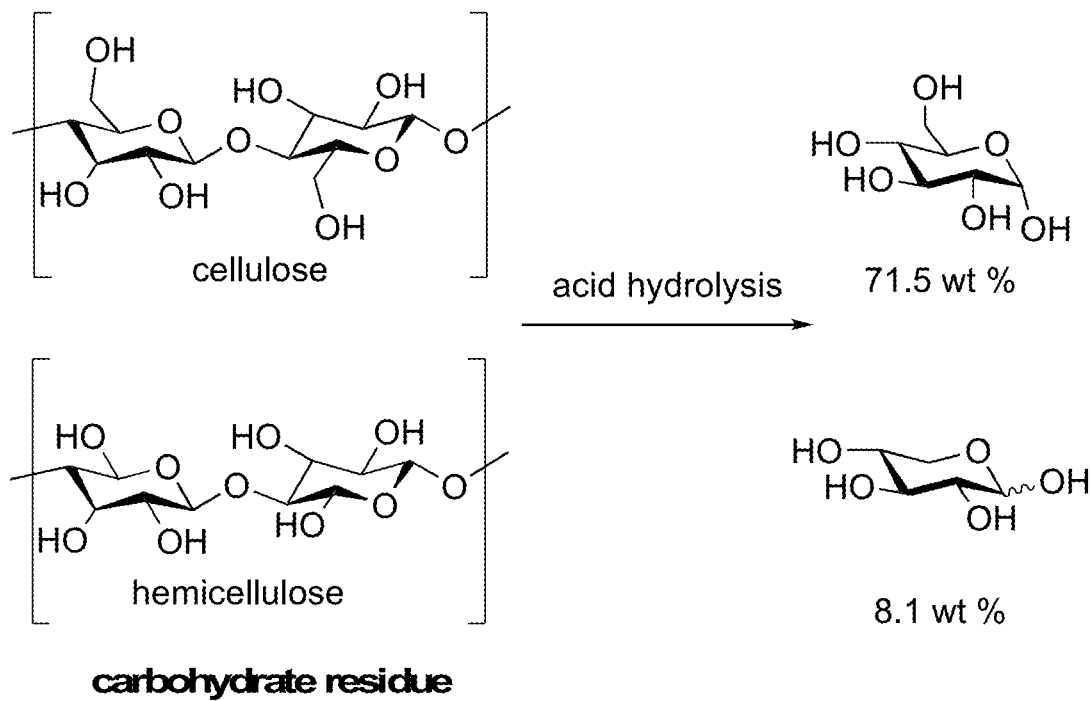

In addition to poplar, other biomass sources are viable starting materials for oxidative catalytic fractionation (FIG. 10, Table 5). Another hardwood, birch, generates the same five monomers in a similar yield to poplar, 25.5 wt %. Pine, a softwood with a lower ratio of S subunits, provides a lower yield of 7.6 wt %, mainly vanillic acid. Miscanthus, a grass, also generates the five monomers observed for poplar, but also produces ferulic and coumaric acids with an overall yield of 11.1 wt %. These results indicate that the oxidative catalytic fractionation chemistry described here is suitable for a range of biomass feedstocks.

corresponding to sugar yields of 83% glucose and 32% xylose from the raw biomass (FIG. 11C). These results show that the carbohydrates from this oxidative catalytic fractionation approach are suitable for a wide array of biorefinery conversion approaches. A full mass balance analysis is discussed below.

Mass Balance of Products from Oxidative Catalytic Fractionation

Figure 12:
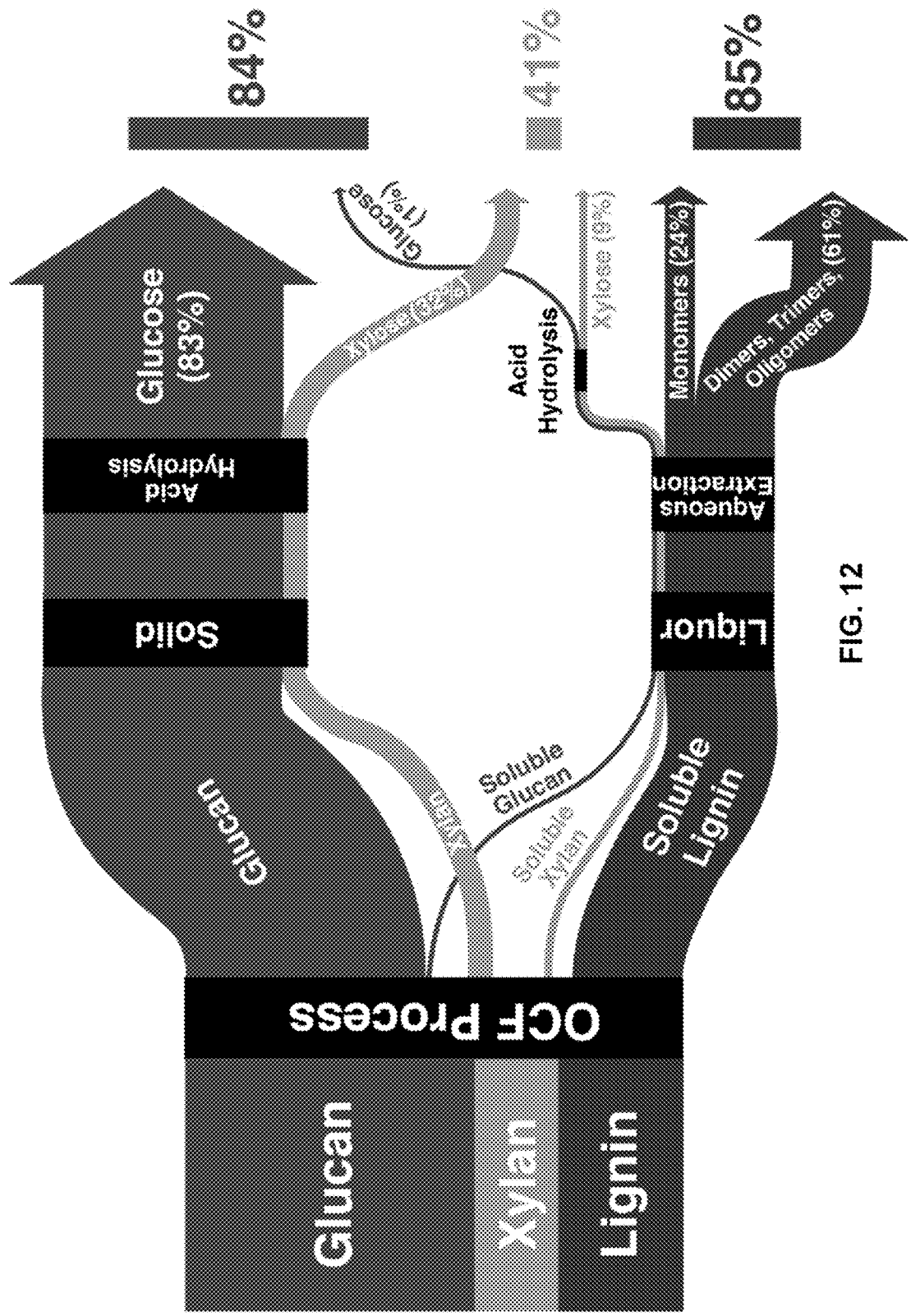
FIG. 12. Mass balance of carbohydrates (glucans+xylans) and lignin of poplar biomass.

For a biomass fractionation approach to be economically viable, not only must good yields of lignin-derived monomers be accessed, but high recoveries of sugars (or sugar-derived products) must also be achievable. We conducted a full mass balance analysis to track to carbohydrate- and lignin-derived products from oxidative catalytic fractionation of poplar (FIG. 12, Table 6). The raw biomass comprised 21.4 wt % lignin, 13.2 wt % hemicellulose, and 45.1 wt % cellulose. After oxidative catalytic fractionation, the solids were filtered off from the solution, and rinsed with acetone. The solution was extracted with water and ethyl acetate. The solid fraction was subjected to acid hydrolysis (vide supra) and generated an 83% yield of glucose and 38% yield of xylose, respective to the cellulose and hemicellulose in the raw biomass. The yield of lignin-derived monomers was quantified by HPLC, corresponding to a 24% yield of monomers, relative to the original lignin. Semi-preparative HPLC was used to separate the lignin-derived oligomers from the monomers, and these oligomers are obtained in a 61% yield by mass. The aqueous layer from the extraction was hydrolyzed with sulfuric acid and analyzed for soluble sugars. Both xylose and glucose were detected, corresponding to yields of 9.4% and 1.7% from the original xylan and glucan, respectively. In total, 85% of the lignin, 84% of the cellulose, and 41% of the hemicellulose is retained through the oxidative catalytic fractionation process.

TABLE 5

Lignin oxidative depolymerization of select biomass sources.[a]
Yields of major phenolic products (weight %)

| Biomass | PHBA[b] | Vanillic acid | Syringic acid | Vanillin | Sa[c] | p-Coumaric acid | Ferulic acid | Total (wt %) |
|---|---|---|---|---|---|---|---|---|
| Poplar | 6.5 | 6.2 | 6.7 | 2.0 | 2.6 | — | — | 24.0 |
| Pine [d] | 0.4 | 4.8 | 1.2 | 0.7 | 0.5 | — | — | 7.6 |
| Birch [e] | 9.1 | 6.8 | 7.1 | 0.7 | 1.8 | — | — | 25.5 |
| Miscanthus [f] | 2.4 | 5.4 | 1.2 | 1.1 | 1.2 | 0.5 | 0.3 | 12.1 |

[a]Reaction conditions: 100 mg biomass, 10 wt % Co-PANI-C, 25 mL acetone, 190° C., 12 h, 35 bar 6% $O_2$.
[b]PHBA = para-hydroxybenzoic acid.
[c]Sa = syringaldehyde.
[d]Lignin content = 22%.
[e]lignin content = 19%.
[f]lignin content = 20%.

Analysis of Carbohydrate Residue

In this oxidative catalytic fractionation process, the carbohydrate residue can be easily obtained post-reaction by simple filtration, due to the use of the catalyst cage to separate the heterogeneous catalyst and biomass. The residue from poplar constitutes 55% of the mass from the starting raw biomass. The solid-state NMR spectra (1D $^{13}C$ cross-polarization magic angle spinning (CPMAS)) of the raw biomass (FIG. 11A) and post-oxidative catalytic fractionation residue (FIG. 11B) show that most of the lignin is removed from the sample (as described above), and that the resonances from the carbohydrates remain consistent. The high quality of the carbohydrate residue is also demonstrated by acid hydrolysis following a modified version of the NREL procedure (Huang et al. 2017). The residue is hydrolyzed to generate 71.5 wt % glucose and 8.1 wt % xylose,

TABLE 6

Compositional analysis of NE 19 and solid residue after reaction.

| | Weight percent of major Components of Biomass | | | | |
|---|---|---|---|---|---|
| | Cellulose | Hemi-cellulose | Lignin | Water | Mass Balance |
| washed NE-19 | 45.1 | 13.2 | 21.4 | 5.6 | 14.7 |
| post-OCF[b] residue[a] | 67.6 | 7.7 | — | 5.6 | 19.1 |

[a]Reaction conditions: 100 mg poplar, 10 wt % Co-PANI-C, 25 mL acetone, 190° C., 12 h, 35 bar 6% $O_2$.
[b]OCF: oxidative catalytic fractionation.

CONCLUSION

We have demonstrated the first example of pH-neutral oxidative catalytic fractionation of raw biomass. This process generates a high-quality carbohydrate residue containing mostly cellulose and a high yield of bifunctional aromatic monomers from lignin. These results highlight the utility of oxidative catalytic fractionation processes in biorefinery applications as a complement to reductive catalytic fractionation or other biomass fractionation approaches.

REFERENCES

Ali, Md. E.; Rahman, Md. M.; Sarkar, S. M.; Hamid, S. B. A., Heterogeneous Metal Catalysts for Oxidation Reactions. Journal of Nanomaterials 2014, Article ID 192038, pp. 1-23.

Anderson, E. M. et al. Flowthrough Reductive Catalytic Fractionation of Biomass. Joule 1, 613-622 (2017).

Anderson, E. M., Stone, M. L., Hulsey, M. J., Beckham, G. T. & Roman-Leshkov, Y. Kinetic Studies of Lignin Solvolysis and Reduction by Reductive Catalytic Fractionation Decoupled in Flow-Through Reactors. ACS Sustainable Chem. Eng. 6, 7951-7959 (2018).

Barth, T.; Kleinert, M., Motor fuels from biomass pyrolysis. Chemical Engineering & Technology: Industrial Chemistry—Plant Equipment—Process Engineering—Biotechnology 2008, 31 (5), 773-781.

Beckham, G. T., Johnson, C. W., Karp, E. M., Salvachúa, D. & Vardon, D. R. Opportunities and challenges in biological lignin valorization. Curr. Opin. Biotech. 42, 40-53 (2016).

Behling, R., Valange, S. & Chatel, G. Heterogeneous catalytic oxidation for lignin valorization into valuable chemicals: what results? What limitations? What trends? Green Chem. 18, 1839-1854 (2016).

Bosque, I., Magallanes, G., Rigoulet, M., Kärkäs, M. D. & Stephenson, C. R. J. Redox Catalysis Facilitates Lignin Depolymerization. ACS Cent. Sci. 3, 621-628 (2017).

Choi, Jong-Ho. (2013). Synthesis and Characterization of Non-precious Metal Co-PANI-C Catalysts for Polymer Electrolyte Membrane Fuel Cell Cathodes. Journal of the Korean Electrochemical Society. 16. 10.5229/JKES.2013.16.1.52.

Das, A. et al. Lignin Conversion to Low-Molecular-Weight Aromatics via an Aerobic Oxidation-Hydrolysis Sequence: Comparison of Different Lignin Sources. ACS Sustainable Chem. Eng. 6, 3367-3374 (2018).

Elangovan, S. et al. From Wood to Tetrahydro-2-benzazepines in Three Waste-Free Steps: Modular Synthesis of Biologically Active Lignin-Derived Scaffolds. ACS Cent. Sci. 5, 1707-1716 (2019).

Gewirth, A. A.; Varnell, J. A.; and DiAscro, A. M., Non-precious Metal Catalysts for Oxygen Reduction in Heterogeneous Aqueous Systems. Chemical Reviews, 2018, 118, 2313-2339.

Hanson, S. K.; Baker, R. T., Knocking on wood: base metal complexes as catalysts for selective oxidation of lignin models and extracts. Accounts of chemical research 2015, 48 (7), 2037-2048.

He, L., Weniger, F., Neumann, H. & Beller, M. Synthesis, Characterization, and Application of Metal Nanoparticles Supported on Nitrogen-Doped Carbon: Catalysis beyond Electrochemistry. Angew. Chem. Int. Ed. 55, 12582-12594 (2016).

Huang, X. et al. Reductive fractionation of woody biomass into lignin monomers and cellulose by tandem metal triflate and Pd/C catalysis. Green Chem. 19, 175-187 (2017).

Jafari, Y., Amiri, H. & Karimi, K. Acetone pretreatment for improvement of acetone, butanol, and ethanol production from sweet sorghum bagasse. Appl. Energy 168, 216-225 (2016).

Jagadeesh, R. V. et al. Selective Oxidation of Alcohols to Esters Using Heterogeneous Co3O4-N@C Catalysts under Mild Conditions. J. Am. Chem. Soc. 135, 10776-10782 (2013).

Kaur, N. & Kishore, D. Catal Sury Asia 2013, 17 (1), 20-42.

Key, R. E.; Bozell, J. J., Progress toward lignin valorization via selective catalytic technologies and the tailoring of biosynthetic pathways. Acs Sustain Chem Eng 2016, 4 (10), 5123-5135.

Klein, I., Marcum, C., Kenttamaa, H. & Abu-Omar, M. M. Mechanistic investigation of the Zn/Pd/C catalyzed cleavage and hydrodeoxygenation of lignin. Green Chem. 18, 2399-2405 (2016).

Koelewijn, S.-F. et al. Promising bulk production of a potentially benign bisphenol A replacement from a hardwood lignin platform. Green Chem. 20, 1050-1058 (2018).

Kumaniaev, I. et al. Lignin depolymerization to monophenolic compounds in a flow-through system. Green Chem. 19, 5767-5771 (2017).

Kumar AK and Sharma S. Recent Updates on Different Methods of Pretreatment of Lignocellulosic Feedstocks: A Review. Bioresour. Bioprocess. (2017) 4:7.

Kumar, P.; Barrett, D. M.; Delwiche, M. J.; Stroeve, P., Methods for Pretreatment of Lignocellulosic Biomass for Efficient Hydrolysis and Biofuel Production. Industrial & Engineering Chemistry Research 2009, 48, (8), 3713-3729.

Lancefield, C. S., Ojo, O. S., Tran, F. & Westwood, N. J. Isolation of Functionalized Phenolic Monomers through Selective Oxidation and C—O Bond Cleavage of the β-O-4 Linkages in Lignin. Angew. Chem. Int. Ed. 54, 258-262 (2015).

Langholtz, M. H., Stokes, B. J. & Eaton, L. M. 2016 Billion-Ton Report: Advancing Domestic Resources for a Thriving Bioeconomy, Volume 1: Economic Availability of Feedstocks. U.S. Department of Energy, Oak Ridge National Laboratory, Oak Ridge, Tenn. (2016). doi: 10.2172/1271651.

Li, C., Zhao, X., Wang, A., Huber, G. W. & Zhang, T. Catalytic Transformation of Lignin for the Production of Chemicals and Fuels. Chem. Rev. 115, 11559-11624 (2015).

Li, C., Zheng, M., Wang, A. & Zhang, T. One-pot catalytic hydrocracking of raw biomass into chemicals over supported carbide catalysts; simultaneous conversion of cellulose, hemicellulose, and lignin. Energy Environ. Sci. 5, 6383-6390 (2012).

Liu, S. et al. Oxidative cleavage of β-O-4 bonds in lignin model compounds with a single-atom Co catalyst. Green Chem. 21, 1974-1981 (2019).

Llevot, A., Grau, E., Carlotti, S., Grelier, S. & Cramail, H. From Lignin-derived Aromatic Compounds to Novel Biobased Polymers. Macromol. Rapid Comm. 37, 9-28 (2016).

Lora, J. Industrial Commercial Lignins: Sources, Properties and Applications. in Monomers, Polymers and Composites from Renewable Resources (eds. Belgacem, M. N. & Gandini, A.) 225-241 (Elsevier Ltd., 2008).

Luo, H.; Wang L. et al. Nitrogen-Doped Carbon-Modified Cobalt-Nanoparticle-Catalyzed Oxidative Cleavage of Lignin β-O-4 Model Compounds under Mild Conditions. ACS Sustainable Chem. Eng. 6, 14188-14196 (2018).

Luo, H. et al. Total Utilization of Miscanthus Biomass, Lignin and Carbohydrates, Using Earth Abundant Nickel Catalyst. ACS Sustainable Chem. Eng. 4, 2316-2322 (2016).

Luo, H.; Abu-Omar, M. M., Lignin extraction and catalytic upgrading from genetically modified poplar. Green Chem 2018, 20 (3), 745-753.

Ma, R., Xu, Y. & Zhang, X. Catalytic Oxidation of Biorefinery Lignin to Value-added Chemicals to Support Sustainable Biofuel Production. ChemSusChem 8, 24-51 (2015).

Mallat, T. & Baiker, A. Oxidation of Alcohols with Molecular Oxygen on Solid Catalysts. Chem. Rev. 104, 3037-3058 (2004).

McKendry, P. Energy production from biomass (part 1): overview of biomass. Bioresource Technol. 83, 37-46 (2002).

Mosier, N. et al. Features of promising technologies for pretreatment of lignocellulosic biomass. Bioresource Technol. 96, 673-686 (2005).

Osterberg, P. et al. Experimental Limiting Oxygen Concentrations for Nine Organic Solvents at Temperatures and Pressures Relevant to Aerobic Oxidations in the Pharmaceutical Industry. Org. Process Res. Dev. 19, 1537-1543 (2015).

Parsell, T. et al. A synergistic biorefinery based on catalytic conversion of lignin prior to cellulose starting from lignocellulosic biomass. Green Chem. 17, 1492-1499 (2015).

Perez, J. M. et al. Funneling aromatic products of chemically depolymerized lignin into 2-pyrone-4-6-dicarboxylic acid with Novosphingobium aromaticivorans. Green Chem. 21, 1340-1350 (2019).

Perras, F. d. r. A.; Luo, H.; Zhang, X.; Mosier, N. S.; Pruski, M.; Abu-Omar, M. M., Atomic-level structure characterization of biomass pre- and post-lignin treatment by dynamic nuclear polarization-enhanced solid-state NMR. The Journal of Physical Chemistry A 2017, 121 (3), 623-630.

Preger, Y. et al. Quinone-Mediated Electrochemical $O_2$ Reduction Accessing High Power Density with an Off-Electrode Co-N/C Catalyst. Joule 2, 2722-2731 (2018).

Rafiee, M., Alherech, M., Karlen, S. D. & Stahl, S. S. J. Am. Chem. Soc. 141, 15266-15276 (2019).

Ragauskas, A. J. et al. Lignin Valorization: Improving Lignin Processing in the Biorefinery. Science, 344, 1246843 (2014).

Ragauskas, A. J.; Williams, C. K.; Davison, B. H.; Britovsek, G.; Cairney, J.; Eckert, C. A.; Frederick, W. J.; Hallett, J. P.; Leak, D. J.; Liotta, C. L., The path forward for biofuels and biomaterials. Science 2006, 311 (5760), 484-489.

Rahimi, A., Azarpira, A., Kim, H., Ralph, J. & Stahl, S. S. Chemoselective Metal-Free Aerobic Alcohol Oxidation in Lignin. J. Am. Chem. Soc. 135, 6415-6418 (2013).

Rahimi, A., Ulbrich, A., Coon, J. J. & Stahl, S. S. Formic-acid-induced depolymerization of oxidized lignin to aromatics. Nature 515, 249-252 (2014).

Renders, T., Van den Bosch, S., Koelewijn, S.-F., Schutyser, W. & Sels, B. F. Lignin-first biomass fractionation: the advent of active stabilisation strategies. Energy Environ. Sci. 10, 1551-1557 (2017).

Renders, T., Van den Bossche, G., Vangeel, T., Van Aelst, K. & Sels, B. Reductive catalytic fractionation: state of the art of lignin-first biorefinery. Curr. Opin. Biotech. 56, 193-201 (2019).

Rinaldi, R. et al. Paving the Way for Lignin Valorisation: Recent Advances in Bioengineering, Biorefining and Catalysis. Angew. Chem. Int. Ed. 55, 8164-8215 (2016).

Sagues, W. J.; Bao, H.; Nemenyi, J. L.; Tong, Z., Lignin-First Approach to Biorefining: Utilizing Fenton's Reagent and Supercritical Ethanol for the Production of Phenolics and Sugars. Acs Sustain Chem Eng 2018, 6 (4), 4958-4965.

Schutyser, W.; Renders, T.; Van den Bosch, S.; Koelewijn, S.-F.; Beckham, G. T.; Sels, B. F. Chemicals from lignin: an interplay of lignocellulose fractionation, depolymerisation, and upgrading. Chem. Soc. Rev. 47, 852-908 (2018).

Schutyser, W.; Kruger, J. S.; Robinson, A. M.; Katahira, R.; Brandner, D. G.; Cleveland, N. S.; Mittal, A.; Peterson, D. J.; Meilan, R.; Roman-Leshkov, Y. Revisiting alkaline aerobic lignin oxidation. Green Chem. 20, 3828-3844 (2018).

Seayad, J.; Saravanan, G.; Ramalingam, B. WO 2017/171652 A1.

Sluiter, A. et al. Determination of Structural Carbohydrates and Lignin in Biomass, Laboratory Analytical Procedure. 2012. NREL Technical Report NREL/TP-510-42618. National Renewable Energy Laboratory, Office of Energy Efficiency and Renewable Energy, U.S. Department of Energy.

Smit, A. & Huijgen, W. Effective fractionation of lignocellulose in herbaceous biomass and hardwood using a mild acetone organosolv process. Green Chem. 19, 5505-5514 (2017).

Song, Q. et al. Lignin depolymerization (LDP) in alcohol over nickel-based catalysts via a fragmentation-hydrogenolysis process. Energy Environ. Sci. 6, 994-1007 (2013).

Song, Y. et al. Gold-catalyzed conversion of lignin to low molecular weight aromatics, Chem. Sci. 9, 8127-8133 (2018).

Strassberger, Z., Tanase, S. & Rothenberg, G. The pros and cons of lignin valorization in an integrated biorefinery. RSC Adv. 4, 25310-25318 (2014).

Sun, T. Tian, B. Su, C. Recent advances in Fe (or Co)/N/C electrocatalysts for the oxygen reduction reaction in polymer electrolyte membrane fuel cells. J. Mater. Chem. A. 5, 18933-18950 (2017).

Sun, Z., Fridrich, B., de Santi, A., Elangovan, S. & Barta, K. Bright Side of Lignin Depolymerization: Toward New Platform Chemicals. Chem. Rev. 118, 614-678 (2018).

Tarabanko, V. E. & Tarabanko, N. Catalytic Oxidation of Lignins into the Aromatic Aldehydes: Genergal Process Trends and Development Prospects. Int. J. Mol. Sci. 18, 2421-2450 (2017).

Tarabanko, V. E., Kaygorodov K. L., et al. Processing pine wood into vanillin and glucose by sequential catalytic oxidation and enzymatic hydrolysis. J. Wood Chem. Tech. 37, 43-51 (2017).

Tuck, C. O., Pérez, E., Horváth, I. T., Sheldon, R. A. & Poliakoff, M. Valorization of Biomass: Deriving More Value from Waste. Science 337, 695-699 (2012).

Upton, B. M.; Kasko, A. M., Strategies for the conversion of lignin to high-value polymeric materials: review and perspective. Chem Rev 2015, 116 (4), 2275-2306.

Van den Bosch, S. et al. Integrating lignin valorization and bio-ethanol production: on the role of Ni—Al2O3 catalyst pellets during lignin-first fractionation. Green Chem. 19, 3313-3326 (2017).

Vangeel, T., Schutyser, W., Renders, T. & Sels, B. F. Perspective on Lignin Oxidation: Advances, Challenges, and Future Directions. Top. Curr. Chem. 376, 30 (2018).

Wang, S., Shuai, L., Saha, B., Vlachos, D. G. & Epps, T. H., III. From Tree to Tape: Direct Synthesis of Pressure Sensitive Adhesives from Depolymerized Raw Lignocellulosic Biomass. ACS Cent. Sci. 2018, 701-708 (2018).

Wu, G.; More, K. L.; Johnston, C. M.; Zelenay, P., High-Performance Electrocatalysts for Oxygen Reduction Derived from Polyaniline, Iron, and Cobale. Science 2011 332, 443-447.

What is claimed is:

1. A method of depolymerizing lignin, the method comprising reacting in a liquid solvent lignocellulosic biomass and an oxidation catalyst with the solvent being in contact with gas comprising $O_2$ gas, wherein the lignocellulosic biomass comprises the lignin and at least one of cellulose and hemicellulose.

2. The method of claim 1, wherein the solvent comprises organic solvent.

3. The method of claim 1, wherein the solvent comprises aprotic solvent.

4. The method of claim 1, wherein the solvent comprises aprotic solvent in an amount of at least about 90% v/v.

5. The method of claim 4, wherein the aprotic solvent is a polar aprotic solvent.

6. The method of claim 1, wherein the solvent is devoid of protic solvent or comprises protic solvent in an amount less than about 10% v/v.

7. The method of claim 1, wherein the solvent comprises a solvent that is not an alcohol and is not water.

8. The method of claim 1, wherein the oxidation catalyst is a heterogeneous catalyst.

9. The method of claim 1, wherein the oxidation catalyst is a metal-based catalyst.

10. The method of claim 1, wherein the oxidation catalyst comprises a metal other than palladium and ruthenium.

11. The method of claim 1, wherein the oxidation catalyst comprises a non-noble metal.

12. The method of claim 1, wherein the oxidation catalyst comprises a first-row transition metal.

13. The method of claim 1, wherein the oxidation catalyst comprises a metal selected from the group consisting of Mn, Fe, Co, Ni, V, and Cu.

14. The method of claim 1, wherein the oxidation catalyst is contained within the solvent within a porous cage.

15. The method of claim 1, wherein the gas comprises $O_2$ gas in an amount from about 1% v/v to about 10% v/v.

16. The method of claim 1, wherein the $O_2$ gas is present at a partial pressure of from about 1 to about 3 bar.

17. The method of claim 1, wherein the reacting is conducted at a temperature from about 100° C. to about 240° C.

18. The method of claim 1, wherein the lignocellulosic biomass comprises the lignin in an amount from about 10% w/w to about 80% w/w of the lignocellulosic biomass and at least one of cellulose in an amount from about 5% w/w to about 90% w/w of the lignocellulosic biomass and hemicellulose in an amount from about 5% w/w to about 90% w/w of the lignocellulosic biomass.

19. The method of claim 1, wherein the reacting is conducted for a time from about 4 hours to about 16 hours.

20. The method of claim 1, wherein the reacting is conducted for a time sufficient to produce a phenolic or benzoquinone monomer.

21. The method of claim 1, wherein the reacting is conducted for a time sufficient to produce a phenolic monomer comprising a benzylic carbonyl.

22. The method of claim 1, wherein the reacting is conducted for a time sufficient to produce p-hydroxybenzoic acid, vanillin, syringaldehyde, vanillic acid, and/or syringic acid.

23. The method of claim 1, further comprising after the reacting, isolating a phenolic monomer produced during the reacting from the solvent.

24. The method of claim 1, further comprising separating from the solvent a carbohydrate residue produced during the reacting.

25. The method of claim 24, wherein the lignocellulosic biomass comprises the lignin in an amount from about 10% w/w to about 80% w/w of the lignocellulosic biomass and at least one of cellulose in an amount from about 5% w/w to about 90% w/w of the lignocellulosic biomass and hemicellulose in an amount from about 5% w/w to about 90% w/w of the lignocellulosic biomass.

26. The method of claim 24, wherein the lignocellulosic biomass has not been treated with any one or more of chemical pretreatment and physicochemical pretreatment.

27. The method of claim 24, wherein the lignin is in the form of raw lignocellulosic biomass.

28. A method of depolymerizing lignin, the method comprising reacting in a liquid solvent the lignin and an oxidation catalyst with the solvent being in contact with gas comprising $O_2$ gas, wherein the solvent is selected from the group consisting of acetone, acetonitrile, and a combination thereof.

29. A method of depolymerizing lignin, the method comprising reacting in a liquid solvent the lignin and an oxidation catalyst with the solvent being in contact with gas comprising $O_2$ gas, wherein the oxidation catalyst comprises a metal-containing nitrogen-doped carbon catalyst.

30. A method of depolymerizing lignin, the method comprising reacting in a liquid solvent lignocellulosic biomass and an oxidation catalyst with the solvent being in contact with gas comprising $O_2$ gas, wherein the lignocellulosic biomass comprises the lignin and has not been treated with any one or more of chemical pretreatment and physicochemical pretreatment.

31. The method of claim 30, wherein the lignin is in the form of raw lignocellulosic biomass.

32. The method of claim 30, wherein:
the solvent comprises an aprotic solvent selected from the group consisting of acetone, acetonitrile, and a combination thereof in an amount of at least about 90% v/v;
the solvent is devoid of protic solvent or comprises protic solvent in an amount less than about 10% v/v;
the oxidation catalyst is a heterogeneous catalyst comprising a metal selected from the group consisting of Mn, Fe, Co, Ni, V, and Cu;
the oxidation catalyst is contained within the solvent within a porous cage;
the gas comprises $O_2$ gas in an amount from about 1% v/v to about 10% v/v;
the $O_2$ gas is present at a partial pressure from about 1 to about 3 bar;
the reacting is conducted at a temperature from about 100° C. to about 240° C.; and the lignocellulosic biomass has not been treated with chemical pretreatment and has not been treated with physicochemical pretreatment.

33. A method of depolymerizing lignin, the method comprising:
- reacting in a liquid solvent the lignin and an oxidation catalyst with the solvent being in contact with gas comprising $O_2$ gas; and
- after the reacting, separating a carbohydrate residue produced during the reacting from the solvent.

\* \* \* \* \*